(12) United States Patent
Howard et al.

(10) Patent No.: US 6,596,741 B2
(45) Date of Patent: Jul. 22, 2003

(54) BIARYL ETHER DERIVATIVES USEFUL AS MONOAMINE REUPTAKE INHIBITORS

(75) Inventors: Harry R. Howard, Bristol, CT (US); Mavis D. Adam, East Lyme, CT (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 10/153,308

(22) Filed: May 22, 2002

(65) Prior Publication Data

US 2003/0055038 A1 Mar. 20, 2003

Related U.S. Application Data

(62) Division of application No. 09/692,335, filed on Oct. 19, 2001, now Pat. No. 6,410,736, which is a continuation of application No. PCT/IB00/01373, filed on Sep. 25, 2000.
(60) Provisional application No. 60/167,761, filed on Nov. 29, 1999.
(51) Int. Cl.$^7$ .................. A61K 31/44; A61K 31/4196; A61K 31/415; A61K 31/381
(52) U.S. Cl. .................. 514/357; 514/383; 514/406; 514/438; 514/471; 514/650; 514/424; 514/327
(58) Field of Search ................. 514/327, 365, 514/357, 383, 407, 424, 438, 471, 650, 717, 466

(56) References Cited

U.S. PATENT DOCUMENTS 5,430,063 A * 7/1995 Ruigt et al. .................. 514/650

* cited by examiner

*Primary Examiner*—Charanjit S. Aulakh
(74) *Attorney, Agent, or Firm*—P. C. Richardson; P. H. Ginsburg; A. D. Joran

(57) ABSTRACT

The present invention relates to compounds of formula I:

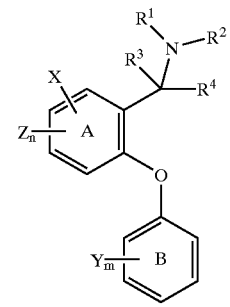

and to their pharmaceutically acceptable salts. Compounds of formula I exhibit activity as serotonin, norepinephrine, and dopamine reuptake inhibitors and can be used in the treatment of central nervous system and other disorders.

4 Claims, No Drawings

BIARYL ETHER DERIVATIVES USEFUL AS MONOAMINE REUPTAKE INHIBITORS

This application claims priority under 35 U.S.C. 120 of U.S. application Ser. No. 09/692,335, filed Oct. 19, 2000, now U.S. Pat. No. 6,410,736. U.S. application Ser. No. 09/692,335 claims priority of PCT/IB00/01373, filed Sep. 25, 2000, which claims priority of U.S. Application No. 60/167,761, filed Nov. 29, 1999.

BACKGROUND OF THE INVENTION

Serotonin Selective Reuptake Inhibitors (SSRIs) currently provide efficacy in the treatment of major depressive disorder (MDD) and are generally perceived by psychiatrists and primary care physicians as effective, well-tolerated and easily administered. However, they are associated with undesirable features, such as reports of sexual dysfunction, delayed onset of action and a level of non-responsiveness estimated to be as high as 30% (see M. J. Gitlin, *Journal of Clinical Psychiatry*, 1994, 55, 406–413 and R. T. Segraves, *Journal of Clinical Psychiatry*, 1992, 10(2), 4–10). Preclinical and clinical evidence has indicated that the sexual dysfunction associated with SSRI therapy can be reduced through the use of dopamine reuptake inhibitors (DRIs), such as bupropion (see A. K. Ashton, *Journal of Clinical Psychiatry*, 1998, 59(3), 112–115). Furthermore, the combination of SRI and DRI may hasten the onset of action as well as offering relief to refractory patients, possibly through a synergistic mechanism (see R. D. Marshall et al, *Journal of Psychopharmacology*, 1995, 9(3), 284–286) and prove beneficial in the treatment of substance abuse and attention deficit hyperactivity disorder (ADHD) according to Barrickman et al, *Journal of the American Academy of Child and Adolescent Psychology*, 1995, 34(5), 649 and Shekim et al, *Journal of Nervous and Mental Disease*, 1989, 177(5), 296.

This invention relates to novel biaryl ether derivatives that exhibit activity as monoamine (e.g., dopamine, serotonin) reuptake inhibitors, to pharmaceutical compositions containing such compounds and to methods of using such compounds to treat central nervous system (CNS) and other disorders.

U.S. Pat. No. 4,018,830, issued Apr. 19, 1997, refers to phenylthioaralkylamines and 2-phenylthiobenzylamines which are active as antiarrhythmics WO 97/17325, International Publication Date May 15, 1997, refers to derivatives of N,N-dimethyl-2-(arylthio) benzylamine which selectively influence serotonin transport in the central nervous system and are useful as antidepressants.

U.S. Pat. No. 5,190,965, issued Mar. 2, 1993, and U.S. Pat. No. 5,430,063, issued Jul. 4, 1995, refer to phenoxyphenyl derivatives which have utility in the treatment of depression.

U.S. Pat. No. 4,161,529, issued Jul. 17, 1979, refers to pyrrolidine derivatives that possess anticholesteremic and hypolipemic activity.

U.S. Provisional Application No. 60/121,313, filed Feb. 23, 1999, refers to biaryl ethers that have activity in inhibiting reuptake of both serotonin and dopamine.

SUMMARY OF THE INVENTION

The present invention relates to compounds of the formula:

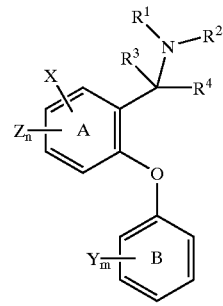

wherein phenyl ring A and phenyl ring B can each, independently, be replaced by a naphthyl group, and wherein when phenyl ring A is replaced by a naphthyl group, the ethereal oxygen of structure I and the carbon to which $R^3$, $R^4$ and $NR^1R^2$ are attached, are attached to adjacent ring carbon atoms of the naphthyl group and neither of said adjacent ring carbon atoms is also adjacent to a fused ring carbon atom of said naphthyl group;

n and m are selected, independently, from one, two and three;

$R^1$ and $R^2$ are selected, independently, from hydrogen, $(C_1-C_4)$alkyl, $(C_2-C_4)$alkenyl, and $(C_2-C_4)$alkynyl, or $R^1$ and $R^2$, together with the nitrogen to which they are attached, form a four to eight membered saturated ring containing one or two heteroatoms, including the nitrogen to which $R^1$ and $R^2$ are attached, wherein the second heteroatom, when present, is selected from oxygen, nitrogen and sulfur, and wherein said ring may optionally be substituted at available binding sites with from one to three substituents selected, independently, from hydroxy and $(C_1-C_6)$alkyl;

$R^3$ and $R^4$ are selected, independently, from hydrogen and $(C_1-C_4)$ alkyl optionally substituted with from one to three fluorine atoms, or $R^3$ and $R^4$ together with the carbon to which they are attached form a four to eight membered saturated carbocyclic ring, and wherein said ring may optionally be substituted at available binding sites with from one to three substituents selected, independently, from hydroxy and $(C_1-C_6)$alkyl;

or $R^2$ and $R^3$, together with the nitrogen to which $R^2$ is attached and the carbon to which $R^3$ is attached, form a four to eight membered saturated ring containing one or two heteroatoms, including the nitrogen to which $R^2$ is attached, wherein the second heteroatom, when present, is selected from oxygen, nitrogen and sulfur, and wherein said ring may optionally be substituted at available binding sites with from one to three substituents selected, independently, from hydroxy and $(C_1-C_6)$alkyl;

each X is selected, independently, from phenyl, heteroaryl (e.g., furan, thiophene, pyrrole, thiazole, isothiazole, oxazole, isoxazole, imidazole, 1,2,4-oxadiazole, 1,2,4-thiadiazole, 1,2,4-triazole, 1,2,3,-triazole, tetrazole, pyridine, pyrimidine, pyrazine, quinoline, isoquinoline, quinazoline, quinoxaline, benzothiophene, benzofuran, benzimidazole, benzisoxazole, benzisothiazole and indole) or heterocycle (e.g., imidazolidine, oxazolidine, thiazolidine, pyrrolidine, piperidine, morpholine) groups as defined below and may be further substituted by hydrogen, halo (i.e., fluorine, chlorine, bromine, iodine), $(C_1-C_4)$alkyl optionally substituted with from one to three fluorine atoms, $(C_1-C_4)$alkoxy optionally substituted with from one to three fluorine atoms, cyano, nitro, amino, hydroxy, carbonyl, $(C_1-C_4)$ alkylamino, di-[$(C_1-C_4)$alkyl]amino, $NR^5(C=O)$ $(C_1-C_4)$alkyl, $SO_2NR^5R^6$ and $SO_p(C_1-C_6)$alkyl, wherein $R^5$ and $R^6$ are selected, independently, from hydrogen and $(C_1-C_6)$alkyl, and p is zero, one or two;

each Y is selected, independently, from hydrogen, halo (i.e., chloro, fluoro, bromo or iodo), $(C_1-C_4)$alkyl optionally substituted with from one to three fluorine atoms, $(C_1-C_4)$alkoxy optionally substituted with from one to three fluorine atoms, cyano, nitro, amino, $(C_1-C_4)$alkylamino, di-[$(C_1-C_4)$alkyl]amino, $NR^5$ $(C=O)(C_1-C_4)$alkyl, $SO_2NR^5R^6$ and $SO_p(C_1-C_6)$ alkyl, wherein $R^5$ and $R^6$ are selected, independently, from hydrogen and $(C_1-C_6)$alkyl, and p is zero, one or two; and each Z is selected independently from hydrogen, halo (i.e., chloro, fluoro, bromo or iodo), $(C_1-C_4)$alkyl optionally substituted with from one to three fluorine atoms, $(C_1-C_4)$alkoxy;

and the pharmaceutically acceptable salts thereof. Compounds of formula I, and their pharmaceutically acceptable salts, have activity in inhibiting reuptake of serotonin, dopamine, and norepinephrine.

In one embodiment of the present invention, ring B is phenyl, not replaced with a naphthyl group. In another embodiment, phenyl ring B in the compounds of formula I is replaced with a naphthyl group.

In a preferred embodiment when ring B is phenyl, each Y is hydrogen or halo. In a more preferred embodiment, m is 1 or 2, and each Y is chlorine.

In another embodiment, the invention relates to compounds of formula I, or pharmaceutically acceptable salts, thereof as described above, but wherein X is selected from furan, thiophene, pyrrole, and 1,2,3-triazole, and wherein X may be further substituted as recited above.

In another embodiment, X is a lactam, for example 1-pyrrolidin-2-one or 1-piperidin-2-one, optionally substituted as recited above and attached to ring A through the lactam nitrogen.

In another embodiment, X is a tetrazole optionally substituted as recited above and attached to ring A through the tetrazole carbon.

In another embodiment, the invention relates to compounds of formula I or salts thereof as described above, but wherein each Z is selected from hydrogen and halo. Preferably, Z is hydrogen.

In a further embodiment, the invention relates to compounds of formula I or salts thereof as described above, wherein $R^3$ and $R^4$ are independently selected from hydrogen and unsubstituted $(C_1-C_4)$ alkyl. Preferably, one or both of $R^3$ and $R^4$ are hydrogen.

In a further embodiment, the invention relates to compounds of formula I or salts thereof, wherein $R^1$ and $R^2$ are independently selected from hydrogen and unsubstituted $(C_1-C_4)$alkyl. Preferably, one of $R^1$ and $R^2$ is hydrogen and the other of $R^1$ and $R^2$ is $(C_1-C_4)$alkyl. More preferably, one of $R^1$ and $R^2$ is hydrogen and the other of $R^1$ and $R^2$ is methyl.

The present invention also relates to a pharmaceutical composition for treating a disorder or condition selected from hypertension, depression (e.g., depression in cancer patients, depression in Parkinson's patients, postmyocardial infarction depression, subsyndromal symptomatic depression, depression in infertile women, pediatric depression, major depression, single episode depression, recurrent depression, child abuse induced depression, and post partum depression), generalized anxiety disorder, phobias (e.g., agoraphobia, social phobia and simple phobias), posttraumatic stress syndrome, avoidant personality disorder, premature ejaculation, eating disorders (e.g., anorexia nervosa and bulimia nervosa), obesity, chemical dependencies (e.g., addictions to alcohol, cocaine, heroin, phenobarbital, nicotine and benzodiazepines), cluster headache, migraine, pain, Alzheimer's disease, obsessive-compulsive disorder, panic disorder, memory disorders (e.g., dementia, amnestic disorders, and age-related cognitive decline (ARCD)), Parkinson's diseases (e.g., dementia in Parkinson's disease, neuroleptic-induced parkinsonism and tardive dyskinesias), endocrine disorders (e.g., hyperprolactinaemia), vasospasm (particularly in the cerebral vasculature), cerebellar ataxia, gastrointestinal tract disorders (involving changes in motility and secretion), negative symptoms of schizophrenia, premenstrual syndrome, fibromyalgia syndrome, stress incontinence, Tourette's syndrome, trichotillomania, kleptomania, male impotence, attention deficit hyperactivity disorder (ADHD), chronic paroxysmal hemicrania and headache (associated with vascular disorders) in a mammal, preferably a human, comprising an amount of a compound of the formula I or a pharmaceutically acceptable salt thereof effective in treating such disorder or condition and a pharmaceutically acceptable carrier.

The present invention also relates to a pharmaceutical composition for treating a disorder or condition that can be treated by inhibiting the reuptake of serotonin, dopamine or norepinephrine in a mammal, preferably a human, comprising an amount of a compound of the formula I, or a pharmaceutically acceptable salt thereof, that is effective in treating such disorder or condition and a pharmaceutically acceptable carrier. Examples of such disorders and conditions are those enumerated in the preceding paragraph.

The present invention also relates to a method for treating a disorder or condition selected from hypertension, depression (e.g., depression in cancer patients, depression in Parkinson's patients, postmyocardial infarction depression, subsyndromal symptomatic depression, depression in infertile women, pediatric depression, major depression, single episode depression, recurrent depression, child abuse induced depression, and post partum depression), generalized anxiety disorder, phobias (e.g., agoraphobia, social phobia and simple phobias), posttraumatic stress syndrome, avoidant personality disorder, premature ejaculation, eating disorders (e.g., anorexia nervosa and bulimia nervosa), obesity, chemical dependencies (e.g., addictions to alcohol, cocaine, heroin, phenobarbital, nicotine and benzodiazepines), cluster headache, migraine, pain, Alzheimer's disease, obsessive-compulsive disorder, panic disorder, memory disorders (e.g., dementia, amnestic disorders, and age-related cognitive decline (ARCD)), Parkinson's diseases (e.g., dementia in Parkinson's disease, neuroleptic-induced parkinsonism and tardive dyskinesias), endocrine disorders (e.g., hyperprolactinaemia), vasospasm (particularly in the cerebral vasculature), cerebellar ataxia, gastrointestinal tract disorders (involving changes in motility and secretion), negative symptoms of schizophrenia, premenstrual syndrome, fibromyalgia syndrome, stress incontinence, Tourette's syndrome, trichotillomania, kleptomania, male impotence, attention deficit hyperactivity disorder (ADHD), chronic paroxysmal hemicrania and headache (associated with vascular disorders) in a mammal, preferably a human, comprising administering to a mammal in need of such treatment an amount of a compound of the formula I, or a pharmaceutically acceptable salt thereof, that is effective in treating such disorder or condition.

The present invention also relates to a method for treating a disorder or condition that can be treated by inhibiting the reuptake of serotonin, dopamine or norepinephrine in a mammal, preferably a human, comprising administering to a mammal in need of such treatment an amount of a compound of the formula I, or a pharmaceutically acceptable salt thereof, that is effective in treating such disorder or condition.

The present invention also relates to a pharmaceutical composition for treating a disorder or condition selected from hypertension, depression (e.g., depression in cancer patients, depression in Parkinson's patients, postmyocardial infarction depression, subsyndromal symptomatic depression, depression in infertile women, pediatric depression, major depression, single episode depression, recurrent depression, child abuse induced depression, and post partum depression), generalized anxiety disorder, phobias (e.g., agoraphobia, social phobia and simple phobias), posttraumatic stress syndrome, avoidant personality disorder, premature ejaculation, eating disorders (e.g., anorexia nervosa and bulimia nervosa), obesity, chemical dependencies (e.g., addictions to alcohol, cocaine, heroin, phenobarbital, nicotine and benzodiazepines), cluster headache, migraine, pain, Alzheimer's disease, obsessive-compulsive disorder, panic disorder, memory disorders (e.g., dementia, amnestic disorders, and age-related cognitive decline (ARCD)), Parkinson's diseases (e.g., dementia in Parkinson's disease, neuroleptic-induced parkinsonism and tardive dyskinesias), endocrine disorders (e.g., hyperprolactinaemia), vasospasm (particularly in the cerebral vasculature), cerebellar ataxia, gastrointestinal tract disorders (involving changes in motility and secretion), negative symptoms of schizophrenia, premenstrual syndrome, fibromyalgia syndrome, stress incontinence, Tourette's syndrome, trichotillomania, kleptomania, male impotence, attention deficit hyperactivity disorder (ADHD), chronic paroxysmal hemicrania and headache (associated with vascular disorders) in a mammal, preferably a human, comprising a serotonin, dopamine or norepinephrine reuptake inhibiting effective amount of a compound of the formula I, or a pharmaceutically acceptable salt thereof, and a pharmaceutically acceptable carrier.

The present invention also relates to a pharmaceutical composition for treating a disorder or condition that can be treated by inhibiting the reuptake of serotonin, norepinephrine or dopamine in a mammal, preferably a human, comprising serotonin, dopamine or norepinephrine reuptake inhibiting effective amount of a compound of the formula I, or a pharmaceutically acceptable salt thereof, and a pharmaceutically acceptable carrier.

The present invention also relates to a method for treating a disorder or condition selected from hypertension, depression (e.g., depression in cancer patients, depression in Parkinson's patients, postmyocardial infarction depression, subsyndromal symptomatic depression, depression in infertile women, pediatric depression, major depression, single episode depression, recurrent depression, child abuse induced depression, and post partum depression), generalized anxiety disorder, phobias (e.g., agoraphobia, social phobia and simple phobias), posttraumatic stress syndrome, avoidant personality disorder, sexual dysfunction (e.g., premature ejaculation), eating disorders (e.g., anorexia nervosa and bulimia nervosa), obesity, chemical dependencies (e.g., addictions to alcohol, cocaine, heroin, phenobarbital, nicotine and benzodiazepines), cluster headache, migraine, pain, Alzheimer's disease, obsessive-compulsive disorder, panic disorder, memory disorders (e.g., dementia, amnestic disorders, and age-related cognitive decline (ARCD)), Parkinson's diseases (e.g., dementia in Parkinson's disease, neuroleptic-induced parkinsonism and tardive dyskinesias), endocrine disorders (e.g., hyperprolactinaemia), vasospasm (particularly in the cerebral vasculature), cerebellar ataxia, gastrointestinal tract disorders (involving changes in motility and secretion), negative symptoms of schizophrenia, premenstrual syndrome, fibromyalgia syndrome, stress incontinence, Tourette's syndrome, trichotillomania, kleptomania, male impotence, attention deficit hyperactivity disorder (ADHD), chronic paroxysmal hemicrania and headache (associated with vascular disorders) in a mammal, preferably a human, comprising administering to a mammal requiring such treatment a serotonin, dopamine or norepinephrine reuptake inhibiting effective amount of a compound of the formula I, or a pharmaceutically acceptable salt thereof.

The present invention also relates to a method for treating a disorder or condition that can be treated by inhibiting the reuptake of serotonin, norepinephrine or dopamine in a mammal, preferably a human, comprising administering to a mammal requiring such treatment a serotonin, dopamine or norepinephrine reuptake inhibiting effective amount of a compound of the formula I, or a pharmaceutically acceptable salt thereof.

The present invention relates to a pharmaceutical composition for treating a condition or disorder that can be treated by inhibiting the reuptake of serotonin, dopamine or norepinephrine in a mammal, preferably a human, comprising:

a) a pharmaceutically acceptable carrier;

b) a compound of the formula I or a pharmaceutically acceptable salt thereof; and c) an NK-1 receptor antagonist or a $5HT_{1D}$ receptor antagonist, or a pharmaceutically acceptable salt thereof;

wherein the amount of the active compounds (i.e., the compound of formula I and the NK-1 receptor antagonist or $5HT_{1D}$ receptor antagonist) are such that the combination is effective in treating such disorder or condition.

The present invention also relates to a method for treating a disorder or condition that can be treated by inhibiting the reuptake of serotonin, dopamine or norepinephrine in a mammal, preferably a human, comprising administering to a mammal requiring such treatment:

a) a compound of the formula I, defined above, or a pharmaceutically acceptable salt thereof; and b) an NK-1 receptor antagonist or a $5HT_{1D}$ receptor antagonist, or a pharmaceutically acceptable salt thereof;

wherein the amounts of the active compounds (i.e., the compound of formula I and the NK-1 receptor antagonist or $5HT_{1D}$ receptor antagonist) are such that the combination is effective in treating such disorder or condition.

This invention also relates to the pharmaceutically acceptable acid addition salts of the compounds of formula I. Examples of pharmaceutically acceptable acid addition salts of the compounds of formula I are the salts of hydrochloric acid, p-toluenesulfonic acid, fumaric acid, citric acid, succinic acid, salicylic acid, oxalic acid, hydrobromic acid, phosphoric acid, methanesulfonic acid, tartaric acid, maleic acid, di-p-toluoyl tartaric acid, acetic acid, sulfuric acid, hydroiodic acid and mandelic acid.

Unless otherwise indicated, the term "halo", as used herein, includes fluoro, chloro, bromo and iodo.

Unless otherwise indicated, the term "alkyl", as used herein, may be straight, branched or cyclic, and may include straight and cyclic moieties as well as branched and cyclic moieties.

Unless otherwise indicated, the term "heteroaryl", as used herein, refers to aromatic groups containing one or more heteroatoms (O, S, or N), preferably from one to four heteroatoms. A multicyclic group containing one or more heteroatoms wherein at least one ring of the group is aromatic is also a "heteroaryl" group for purposes of the present invention, unless otherwise indicated. The heteroaryl groups of the compounds of this invention can also include ring systems substituted with one or more oxo moieties. Examples of heteroaryl groups are pyridinyl, pyridazinyl, imidazolyl, pyrimidinyl, pyrazolyl, triazolyl, pyrazinyl, quinolyl, isoquinolyl, tetrazolyl, furyl, thiophenyl, isoxazolyl, thiazolyl, oxazolyl, isothiazolyl, pyrrolyl, indolyl, benzimidazolyl, benzofuranyl, cinnolinyl, indazolyl, indolizinyl, phthalazinyl, triazinyl, isoindolyl, purinyl, oxadiazolyl, thiadiazolyl, furazanyl, benzofurazanyl, benzothiophenyl, benzotriazolyl, benzothiazolyl, benzisothiazolyl, benzoxazolyl, benzisoxazolyl, benzimidazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl, and azaindolyl.

The term "heterocycle", as used herein and unless otherwise indicated, refers to non-aromatic cyclic groups containing one or more heteroatoms, prefereably from one to four heteroatoms, each selected from O, S and N. "Heterocycle", unless otherwise indicated, includes heterobicycle groups. "Heterobicycle" refers to non-aromatic two-ringed cyclic groups, wherein said rings share one or two atoms, and wherein at least one of the rings contains a heteroatom (O, S, or N). Heterobicycle groups for purposes of the present invention, and unless otherwise indicated, include spiro groups and fused ring groups. In one embodiment, each ring in the heterobicycle contains up to four heteroatoms (i.e. from zero to four heteroatoms, provided that at least one ring contains at least one heteroatom). The heterocyclic groups of this invention can also include ring systems substituted with one or more oxo moieties. Examples of heterocycle groups include, but are not limited to, aziridinyl, azetidinyl, pyrrolidinyl, piperidinyl, azepinyl, piperazinyl, 1,2,3,6-tetrahydropyridinyl, oxiranyl, oxetanyl, tetrahydrofuranyl, tetrahydrothienyl, tetrahydropyranyl, tetrahydrothiopyranyl, oxazolidinyl, morpholino, thiomorpholino, thiazolidinyl, thioxanyl, pyrrolinyl, indolinyl, 2H-pyranyl, 4H-pyranyl, dioxanyl, 1,3-dioxolanyl, pyrazolinyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, quinolizinyl, quinuclidinyl, 1,4-dioxaspiro[4.5]decyl, 1,4-dioxaspiro[4.4]nonyl, 1,4-dioxaspiro[4.3]octyl, and 1,4-dioxaspiro[4.2]heptyl.

The foregoing groups, heteroaryl or heterocycle, may be C-attached or N-attached where such is possible. For instance, a group derived from pyrrole may be pyrrol-1-yl (N-attached) or pyrrol-3-yl (C-attached). The terms referring to the groups also encompass all possible tautomers.

When reference is made to $SO_p(C_1–C_6)$alkyl, and p is two, this indicates a sulfone, in other words, $S(=O)_2$$(C_1–C_6)$alkyl.

The terms "treatment", "treating", and the like, refers to reversing, alleviating, or inhibiting the progress of the disease or condition to which such term applies, or one or more symptoms of such disease or condition. As used herein, these terms also encompass, depending on the condition of the patient, preventing a disease or condition, including preventing the onset of a disease or condition, or of symptoms associated with a disease or condition, and including reducing the severity of a disease or condition or symptoms associated therewith prior to affliction with said disease or condition. Such prevention or reduction prior to affliction refers to administration of the compound of the invention to a subject that is not at the time of administration afflicted with the disease or condition. "Preventing" also encompasses preventing the recurrence of a disease or condition or of symptoms associated therewith.

The term "mammal", as used herein, refers to any member of the class "Mammalia", including, but not limited to, humans, dogs, and cats.

When reference is made herein to a disorder or condition that can be treated by inhibiting the reuptake of serotonin, dopamine, or norepinephrine, this means that the disorder or condition has as a contributing factor at least one of serotonin, dopamine, or norepinephrine-mediated neurotransmission. The disorder or condition may have as a contributing factor one, two, or all three of the aforementioned types of neurotransmission. Moreover, a factor or factors other than serotonin, dopamine, or norepinephrine-mediated neurotransmission may also contribute to the disorder or condition. Disorders and conditions to which serotonin, dopamine, or norepinephrine-mediated neurotransmission contribute can be ascertained by those of ordinary skill in the art and include, but are not limited to, for example, addiction and substance abuse, depression, and phobia.

The compounds of formula I may have optical centers and therefore may occur in different enantiomeric configurations. The invention includes all enantiomers, diastereomers, and other stereoisomers of such compounds of formula I, as well as racemic and other mixtures thereof. The invention also includes tautomers of compounds of formula I.

The subject invention also includes isotopically-labeled compounds, which are identical to those recited in formula I, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine, iodine, and chlorine, such as $^3H$, $^{11}C$, $^{14}C$, $^{18}F$, $^{123}I$ and $^{125}I$. Compounds of the present invention and pharmaceutically acceptable salts of said compounds that contain the aforementioned isotopes and/or other isotopes of other atoms are within the scope of this invention. Isotopically-labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of formula I of this invention can generally be prepared by carrying out the procedures disclosed in the Schemes and/or in the Examples below, by substituting a readily available isotopically labeled reagent for a non-isotopically labeled reagent.

"Chemical dependency," as used herein, means an abnormal craving or desire for, or an addiction to a drug. Such drugs are generally administered to the affected individual by any of a variety of means of administration, including oral, parenteral, nasal or by inhalation. Examples of chemical dependencies treatable by the methods of the present invention are dependencies on alcohol, nicotine, cocaine, heroin, phenolbarbitol, and benzodiazepines (e.g., Valium (trademark)). "Treating a chemical dependency," as used herein, means reducing or alleviating such dependency.

An NK-1 receptor antagonist, as recited herein, is a substance that is able to antagonize NK-1 receptors, thereby inhibiting tachykinin-mediated responses, such as responses mediated by substance P. Various NK-1 receptor antagonists are known in the art, and any such NK-1 receptor antagonist can be utilized in the present invention as described above in combination with a compound of formula I. NK-1 receptor antagonists are described in, for example, U.S. Pat. No. 5,716,965 (issued Feb. 10, 1998); U.S. Pat. No. 5,852,038 (issued Dec. 22, 1998); WO 90/05729 (International Publication Date May 31, 1990); U.S. Pat. No. 5,807,867 (issued Sep. 15, 1998); U.S. Pat. No. 5,886,009 (issued Mar. 23, 1999); U.S. Pat. No. 5,939,433 (issued Aug. 17, 1999); U.S. Pat. No. 5,773,450 (issued Jun. 30, 1998); U.S. Pat. No. 5,744,480 (issued Apr. 28, 1998); U.S. Pat. No. 5,232,929 (issued Aug. 3, 1993); U.S. Pat. No. 5,332,817 (issued Jul. 26, 1994); U.S. Pat. No. 5,122,525 (issued Jun. 16, 1992); U.S. Pat. No. 5,843,966 (issued Dec. 1, 1998); U.S. Pat. No. 5,703,240 (issued Dec. 30, 1997); U.S. Pat. No. 5,719,147 (issued Feb. 17, 1998); and U.S. Pat. No. 5,637,699 (issued Jun. 10, 1997). Each of the foregoing U.S. patents and the foregoing published PCT International Application are incorporated in their entireties herein by reference. The compounds described in said references having NK-1 receptor antagonizing activity can be used in the present invention. However, other NK-1 receptor antagonists can also be used in this invention.

A $5HT_{1D}$ receptor antagonist, as recited herein, is a substance that antagonizes the $5HT_{1D}$ subtype of serotonin receptor. Any such substance can be used in the present invention as described above in combination with a compound of formula I. Substances having $5HT_{1D}$ receptor antagonizing activity can be determined by those of ordinary skill in the art. For example, $5HT_{1D}$ receptor antagonists are described in WO 98/14433 (International Publication Date Apr. 9, 1998); WO 97/36867 (International Publication Date Oct. 9, 1997); WO 94/21619 (International Publication Date Sep. 29, 1994); U.S. Pat. No. 5,510,350 (issued Apr. 23, 1996); U.S. Pat. No. 5,358,948 (issued Oct. 25, 1994); and GB 2276162 A (published Sep. 21, 1994). These $5HT_{1D}$ receptor antagonists, as well as others, can be used in the present invention. The aforementioned published patent applications and patents are incorporated herein by reference in their entireties.

Preferred embodiments of this invention include the following compounds of the formula I and their pharmaceutically acceptable salts:

[4-(3,4-Dichlorophenoxy)-biphenyl-3-ylmethyl]-methylamine,

[2-(3,4-Dichlorophenoxy)-5-thiophen-3-ylbenzyl]-methylamine,

[2-(3,4-Dichlorophenoxy)-4-thiophen-3-ylbenzyl]-methylamine,

[2-(3,4-Dichlorophenoxy)-4-furan-2-ylbenzyl]-methylamine,

[2-(3,4-Dichlorophenoxy)-5-furan-2-ylbenzyl]-methylamine,

N-[4'-(3,4-Dichlorphenoxy)-3'-methylaminomethyl-biphenyl-3-yl]-acetamide,

[2-(3,4-Dichlorophenoxy)-5-thiophen-2-ylbenzyl]-methylamine,

[4-(3,4-Dichlorophenoxy)-4'-fluoro-biphenyl-3-ylmethyl]-methyamine,

[2-(3,4-Dichlorophenoxy)-5-[1,2,3]triazol-1-ylbenzyl]-methylamine,

[2-(3,4-Dichlorophenoxy)-5-[1,2,3]triazol-2-ylbenzyl]-methylamine,

[2-(3,4-Dichlorophenoxy)-5-pyridin-2-ylbenzyl]-methylamine,

[2-(3,4-Dichlorophenoxy)-5-pyridin-3-ylbenzyl]-methylamine,

1-[4-(3,4-Dichlorophenoxy)-3-methylaminomethylphenyl]-1H-pyrazol-3-ylamine,

[2-(3,4-Dichlorophenoxy)-5-pyridin-4-ylbenzyl]-methylamine,

[3-(3,4-Dichlorophenoxy)-biphenyl-4-ylmethyl]-methylamine,

[4-(3,4-Dichlorophenoxy)-4'-methyl-biphenyl-3-ylmethyl]-methylamine, and

[2-(3,4-Dichlorophenoxy)-4-thiophen-2-ylbenzyl]-methylamine.

Other preferred embodiments of this invention include the following compounds and their pharmaceutically acceptable salts:

[2-(3,4-dichlorophenoxy)-5-thiazol-2-ylbenzyl]-methylamine;

[2-(3,4-dichlorophenoxy)-5-(1H-tetrazol-5-yl)benzyl]-methylamine;

[2-(3,4-dichlorophenoxy)-5-furan-3-ylbenzyl]-methylamine;

{1-[2-(3,4-dichlorophenoxy)-5-[1,2,3]triazol-1-ylphenyl]ethyl}-methylamine;

{1-[2-(3,4-dichlorophenoxy)-5-[1,2,3]triazol-2-ylphenyl]ethyl}-methylamine;

{1-[2-(3,4-dichlorophenoxy)-5-thiazol-2-ylphenyl]ethyl}-methylamine;

{1-[2-(3,4-dichlorophenoxy)-4-[1,2,4]triazol-1-ylphenyl]ethyl}-methylamine;

[2-(3,4-dichlorophenoxy)-5-(5-methylthiophen-2-yl)benzyl]-methylamine;

[2-(3,4-dichlorophenoxy)-5-[1,2,4]triazol-4-ylbenzyl]-methylamine;

1-[4-(3,4-dichlorophenoxy)-3-(methylaminomethyl)phenyl]-pyrrolidin-2-one;

1-[4-(3,4-dichlorophenoxy)-3-(1-methylaminoethyl)phenyl]-pyrrolidin-2-one; and

1-[4-(3,4-dichlorophenoxy)-3-(methylaminomethyl)
phenyl]-piperidin-2-one.

Other embodiments of this invention include the following compounds and their pharmaceutically acceptable salts:

[2-(3,4-dichlorophenoxy)-5-pyrimidin-2-ylbenzyl]-methylamine,

[2-(3,4-dichlorophenoxy)-5-pyrimidin-4-ylbenzyl]-methylamine,

[2-(3,4-dichlorophenoxy)-5-(2-methylpyrimidin-4-yl)-benzyl]-methylamine,

{1-[2-(3,4-dichlorophenoxy)-5-(2-methylpyrimidin-4-yl)-phenyl]-ethyl}-methylamine, 4-[4-(3,4-dichlorophenoxy)-3-(1-methylpyrrolidin-2-yl)-phenyl]-2-methylpyrimidine,

[2-(4-chlorophenoxy)-5-(1-methyl-1H-pyrrol-3-yl)-benzyl]-dimethylamine,

[5-(1-methyl-1H-pyrrol-3-yl)-2-(naphthalen-2-yloxy)-benzyl]-dimethyl amine,

[5-imidazol-1-yl-2-(naphthalen-2-yloxy)-benzyl]-dimethylamine, 1,5,5-trimethyl-3-[3-methylaminomethyl-4-(naphthalen-2-yloxy)-phenyl]-imidazolidine-2,4-dione, 1-methyl-3-[3-methylaminomethyl-4-(naphthalen-2-yloxy)-phenyl]-imidazolidine-2,4-dione, 3-[3-methylaminomethyl-4-(naphthalen-2-yloxy)-phenyl]-thiazolidine-2,4-dione, 3-[3-methylaminomethyl-4-(naphthalen-2-yloxy)-phenyl]-oxazolidine-2,4-dione, 3-[3-methylaminomethyl-4-(naphthalen-2-yloxy)-phenyl]-oxazolidin-2-one, 3-[3-methylaminomethyl-4-(naphthalen-2-yloxy)-phenyl]-thiazolidin-2-one, 1-methyl-3-[3-methylaminomethyl-4-(naphthalen-2-yloxy)-phenyl]-imidazolidin-2-one, 1-methyl-3-[3-methylaminomethyl-4-(naphthalen-2-yloxy)-phenyl]-tetrahydro-pyrimidin-2-one, 1-[4-(3,4-dichlorophenoxy)-3-methylaminomethyl-phenyl]-3-methyl-tetrahydropyrimidin-2-one, 1-[4-(3,4-dichlorophenoxy)-3-methylaminomethyl-phenyl]-3-methylimidazolidin-2-one, 3-[4-(3,4-dichlorophenoxy)-3-methylaminomethyl-phenyl]-thiazolidin-2-one, 3-[4-(3,4-dichlorophenoxy)-3-methylaminomethyl-phenyl]-oxazolidin-2-one,

[2-(3,4-dichlorophenoxy)-5-(2-methylthiazol-4-yl)-benzyl]-methylamine,

[2-(3,4-dichlorophenoxy)-5-(2-methyloxazol-4-yl)-benzyl]-methylamine,

[2-(3,4-dichlorophenoxy)-5-(2,5-dimethyloxazol-4-yl)-benzyl]-methylamine,

[2-(3,4-dichlorophenoxy)-5-(2,5-dimethylthiazol-4-yl)-benzyl]-methylamine,

[2-(3,4-dichlorophenoxy)-5-(5-methyl-[1,2,4]thiadiazol-3-yl)-benzyl]-methylamine,

[2-(3,4-dichlorophenoxy)-5-(5-methyl-[1,2,4]oxadiazol-3-yl)-benzyl]-methylamine,

[2-(3,4-dichlorophenoxy)-5-[1,2,3]oxadiazol-4-yl-benzyl]-methylamine,

[2-(3,4-dichlorophenoxy)-5-(5-methyl-[1,2,3]thiadiazol-4-yl)-benzyl]-methylamine,

[2-(3,4-dichlorophenoxy)-5-(2,4-dimethyloxazol-5-yl)-benzyl]-methylamine,

[2-(3,4-dichlorophenoxy)-5-(2,4-dimethylthiazol-5-yl)-benzyl]-methylamine,

[2-(3,4-dichlorophenoxy)-5-[1,2,4]triazol-1-ylbenzyl]-methylamine,

[2-(3,4-dichlorophenoxy)-5-(3-methyl-[1,2,4]triazol-1-yl)-benzyl]-methylamine,

[2-(4-chlorophenoxy)-5-(3,5-dimethyl-[1,2,4]triazol-1-yl)-benzyl]-methylamine,

[2-(4-chlorophenoxy)-5-tetrazol-1-ylbenzyl]-methylamine,

[2-(4-chlorophenoxy)-5-(5-methyltetrazol-1-yl)-benzyl]-dimethylamine,

[2-(4-chlorophenoxy)-5-[1,2,4]triazol-4-ylbenzyl]-dimethylamine,

[2-(4-chlorophenoxy)-5-(1-methyl-1H-tetrazol-5-yl)-benzyl]-dimethylamine, and

{1-[2-(3,4-dichlorophenoxy)-5-(1-methyl-1H-tetrazol-5-yl)-phenyl]-ethyl}-dimethylamine.

This invention also relates to compounds of the formula:

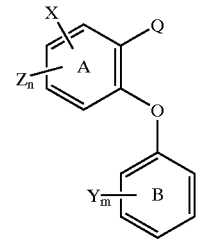

XVIII wherein X, Z, Y, n, and m are defined as above and Q is —C(=O)R³ or cyano and R³ is H, $C_1$–$C_4$ alkyl, OH, O—($C_1$–$C_6$)alkyl or $NR^1R^2$, wherein $R^1$ and $R^2$ are selected, independently, from hydrogen and ($C_1$–$C_4$) alkyl, or $R^1$ and $R^2$, together with the nitrogen to which they are attached, form a four to eight membered saturated ring containing one or two heteroatoms, including the nitrogen to which $R^1$ and $R^2$ are attached, wherein the second heteroatom, when present, is selected from oxygen, nitrogen and sulfur. Compounds of formula XVIII are useful as intermediates for preparing compounds of formula I.

The compounds of formula XVIII may have optical centers and therefore may occur in different enantiomeric configurations. The invention includes all enantiomers, diastereomers, and other stereoisomers of such compounds of formula XVIII, as well as racemic and other mixtures thereof. The invention also includes tautomers of compounds of formula XVIII.

DETAILED DESCRIPTION OF THE INVENTION

Compounds of the formula I may be prepared according to the following reaction Schemes and discussion. Unless otherwise indicated, A, B, Q, $R^1$, $R^2$, $R^3$, $R^4$, $R^5$, $R^6$, X, Y, Z, m and n, and structural formulas I and XVIII, in the reaction schemes and discussion that follows are as defined above.

SCHEME 1
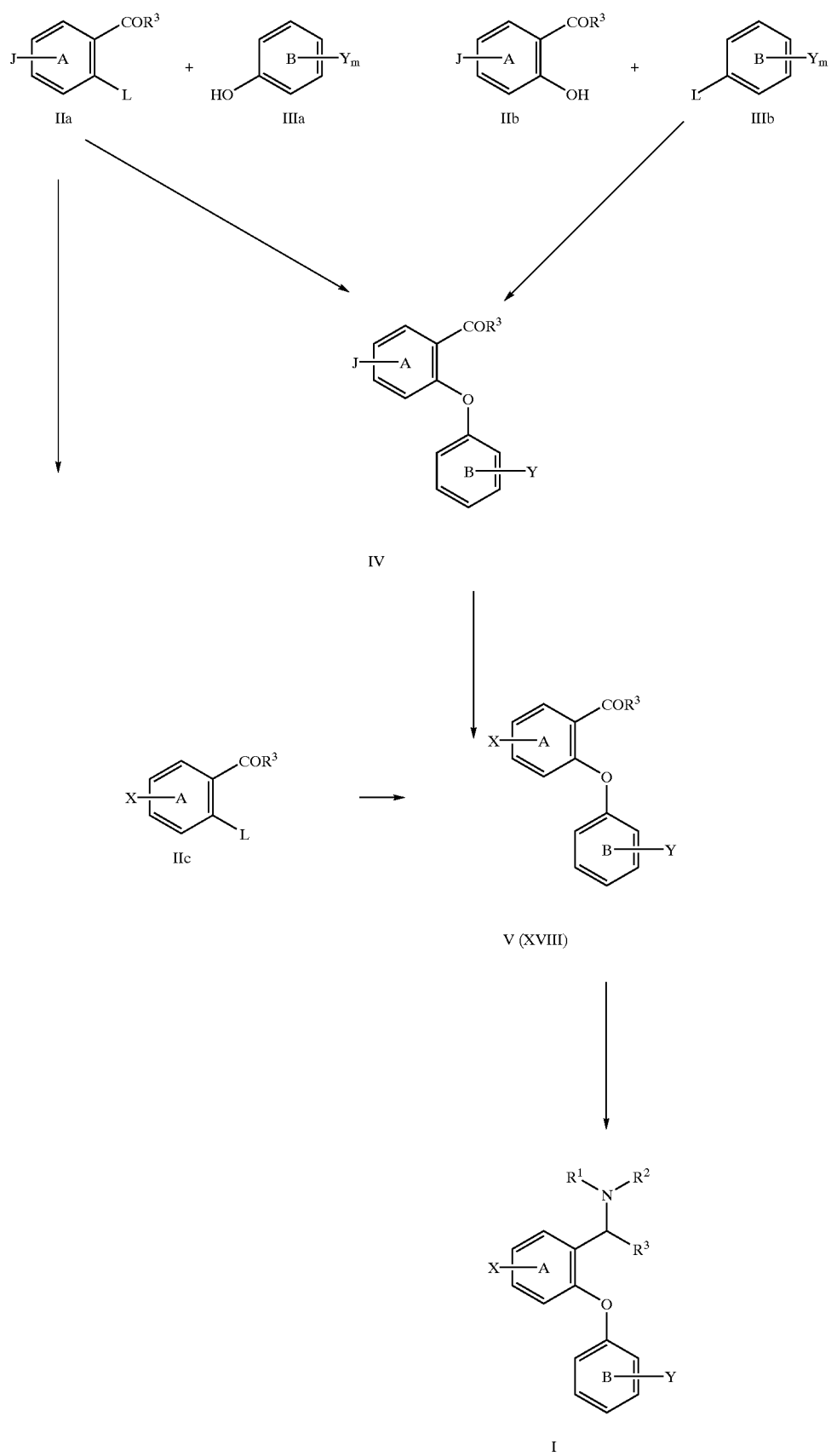

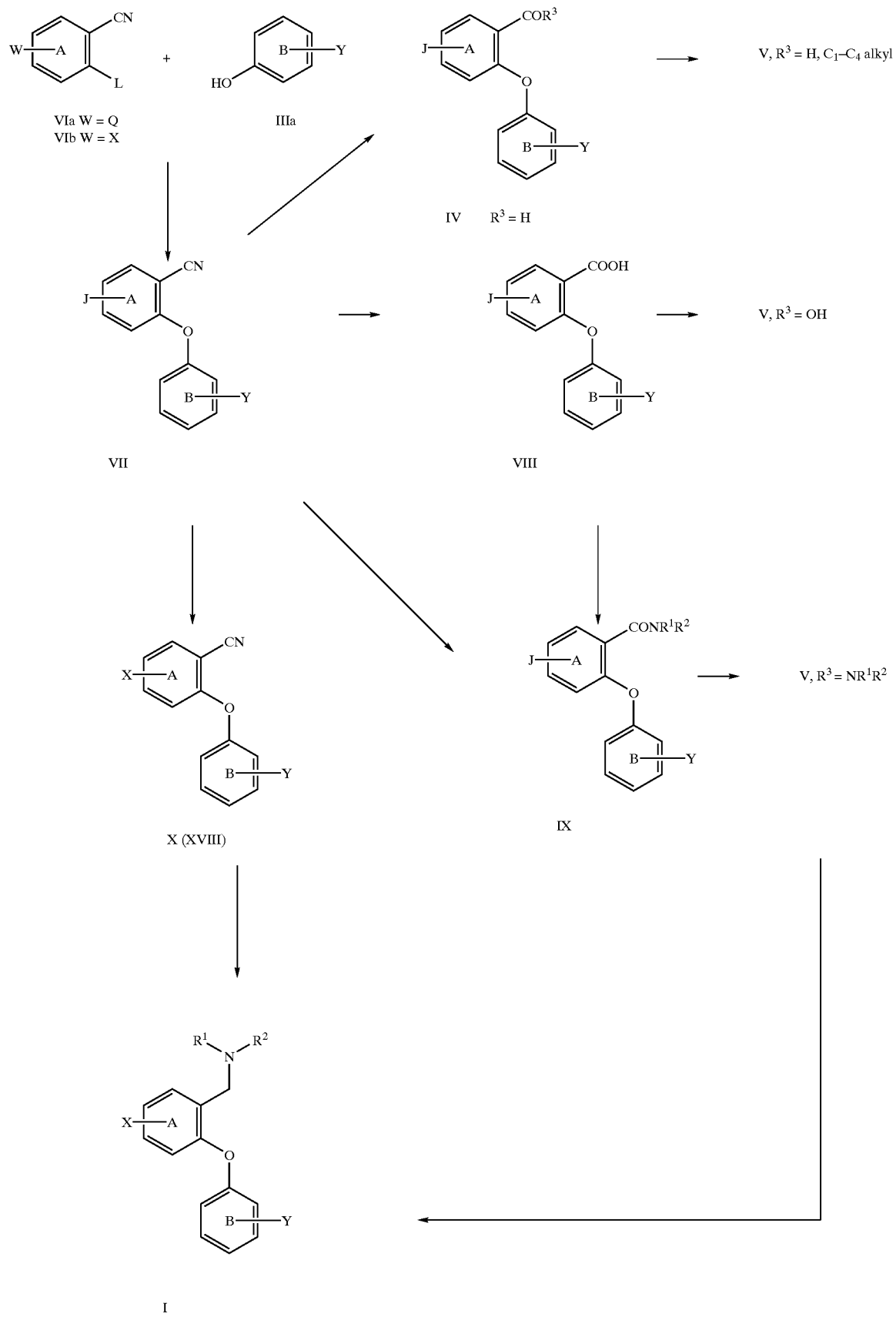
SCHEME 2

SCHEME 3

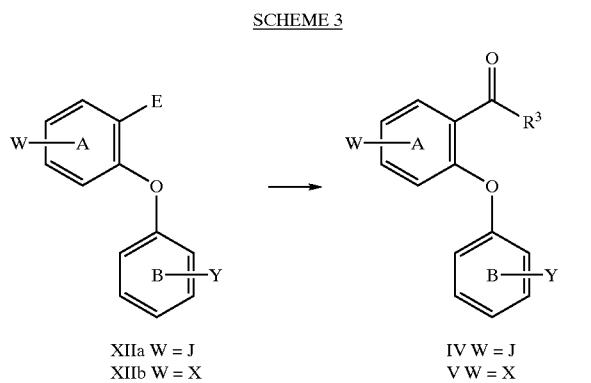

XIIa W = J
XIIb W = X

IV W = J
V W = X

SCHEME 4

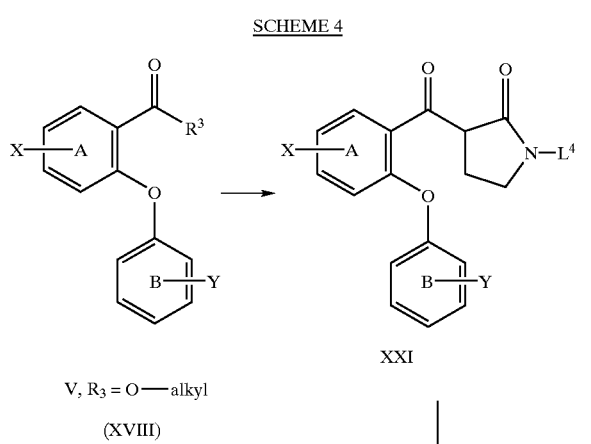

V, R₃ = O—alkyl
(XVIII)

XXI

XXII

XXIII

Scheme 5

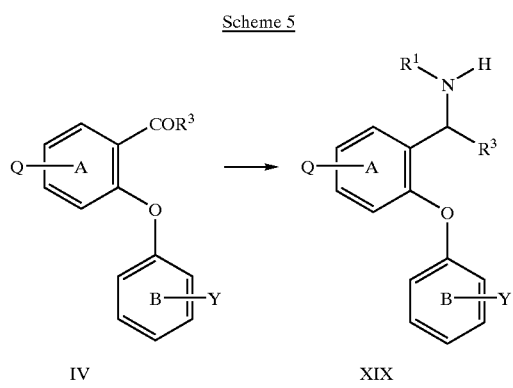

IV

XIX

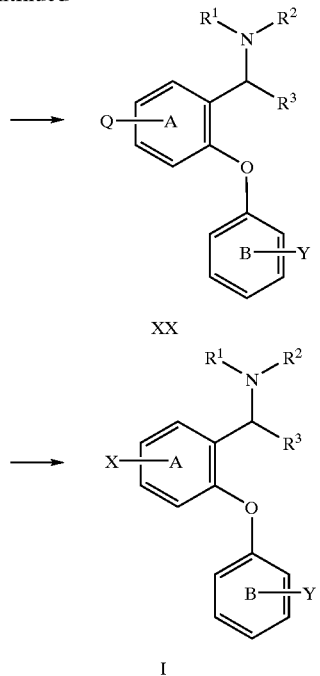

XX

I

Scheme 1 refers to the preparation of compounds of the formula I from compounds of the formulae II and III. L represents a suitable leaving group such as flouro, chloro, nitro, or triflate. In scheme 1, Z is hydrogen. However, using the appropriate starting compound of formula II, compounds of formula I wherein Z is other than hydrogen can be prepared according to the same scheme. Compounds of the formulas IIa, IIb, IIIa and IIIb are commercially available or can be made by methods well known to those of ordinary skill in the art. For example, compounds of general formulas IIa and IIb wherein $R^3$ is H may be prepared by introducing an aldehyde functional group (CHO) to a compound of formula XV or XVI, respectively, using methods well known to those of skill in the art.

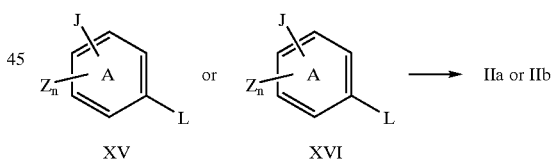

XV                XVI

When L=F, the procedure of A. J. Bridges et al., *Tetrahedron Letters*, 1992, 33(49), 7499–7502, is particularly useful for the synthesis of substituted ortho-fluorobenzaldehydes. Other such transformations have been described by C. F. H. Allen et al., *Organic Synthesis*, 1951, 31, 92; T. DePaulis et al, *Journal of Medicinal Chemistry*, 1986, 29, 61; I. M. Godfrey et al., J. Chemical Society, Perkin Transactions 1, 1974, 1353; K. M. Tramposil et al., *Journal of Medicinal Chemistry*, 1983, 26(2), 121; and M. E. Cracknell et al., *Chemistry and Industry*, (London), 1985, (9), 309.

Referring to Scheme 1, a compound (i.e., an aldehyde or ketone) of the formula IIa is reacted with a compound (i.e., a phenol) of the formula IIIa in the presence of a base to form the corresponding compound of formula IV. This reaction is generally carried out at a temperature from about 0° C. to about 150° C. for about 1 hour to about 3 days, preferably at about 90–95° C. for about 18 hours, in a polar solvent such as dimethyl sulfoxide (DMSO), N,N-dimethylformamide (DMF), N,N-dimethylacetamide (DMA) or N-methyl-2-pyrrolidinone (NMP), preferably DMF. Suitable bases include anhydrous sodium carbonate ($Na_2CO_3$), potassium carbonate ($K_2CO_3$), sodium hydroxide (NaOH), potassium hydroxide (KOH) and amines such as pyrrolidine, triethylamine and pyridine, with anhydrous $K_2CO_3$ being preferred. Details for conducting this procedure can be found in G. W. Yeager et al., *Synthesis*, 1995, 28–30; J. R. Dimmock et al., *Journal of Medicinal Chemistry*, 1996, 39(20), 3984–3997. Alternatively, phenols of the formula IIb and compounds of the formula IIIb may be converted into aldehydes or ketones of the general formulae IV according to the procedures described by K. Tomisawa et al., *Chemical and Pharmaceutical Bulletin*, 1984, 32(8), 3066–3074.

Next, a compound of the formula IV, wherein J is a leaving group, for example bromine, iodine, triflate, fluorosulfonate or methanesulfonate, can be converted to a compound of the formula V by reaction with a compound of the general formula X-G, wherein G is defined as a reactive leaving group such as $B(OH)_2$, $Sn[(C_1-C_6)alkyl]$, $Zn(Hal)$ and the like, usually in the presence of a catalytic amount of a catalyst, e.g., tetrakis(triphenylphosphine) palladium(0), tetrakis(triphenylphosphine) nickel(0) or dichlorobis(triphenylphosphine) palladium(II), among others, and in the presence of a base such as sodium carbonate, potassium carbonate or triethylamine. The reactions can be conducted in a variety of organic solvents (e.g., benzene, dimethoxyethane) or in mixtures such as aqueous N,N-dimethylformamide or aqueous ethanol at temperatures in the range of about 0° C. to about 100° C. A good general reference for this process may be found in the review by Stephen Stanforth, *Tetrahedron*, 1998, 54, 263–303. Other specific references include M. J. Sharp et al, *Synthetic Communications*, 1981, 11(7), 513; R. B. Miller et al, *Tetrahedron Letters*, 1989, 30(3), 297; W. J. Thompson et al, *Journal of Organic Chemistry*, 1984, 49(26), 5237. The compounds of the general formula X-G are in many cases commercially available or can be prepared by one skilled in the art of organic synthesis (for example, see the procedures in M. J. Sharp and V. Snieckus, *Tetrahedron Letters*, 1985, 26(49), 5997–6000; G. W. Kabalka et al, *Journal of Organometallic Chemistry*, 1983, 259, 269–274).

Alternatively, an intermediate of the formula IIa may be converted into a compound of the formula IIc, wherein X is as defined above, using the methods described above for the conversion of compounds of formula IV to V. These intermediates of formula IIc can then be reacted with a compound of the general formula IIIa to produce the ethers of general formula V using the methods described above for the conversion of compounds of formula IIa to IV.

Additionally, compounds of formulae IIa or IV, wherein J is a functional group like CN, can be converted to compounds of the formula IIc or V wherein X is a moiety such as:

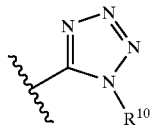

and wherein $R^{10}$ is independently chosen from hydrogen, $(C_1-C_6)$alkyl, aryl-$(C_1-C_6)$alkyl or aryl, optionally substituted with hydrogen, halo, $(C_1-C_6)$alkyl, $(C_1-C_6)$alkoxyl or $(C_1-C_6)SO_r$, where r is zero, one or two. Methods for this conversion are well documented in the chemical literature; for example, through the use of sodium azide and lithium chloride in 2-methoxyethanol according to the procedure described by J. Sauer et al, *Tetrahedron*, 1960, 11, 241. Under these conditions, it may be necessary to initially protect the $COR^3$ group of compound IIa or IV to effectively convert the J group to the corresponding group X of compounds IIc or V (intermediates of formula XVIII), respectively. There are many protecting groups available which can be utilized in this process, including acetals and ketals which are described and referenced by P. G. M. Wuts and T. W. Green in *Protective Groups in Organic Synthesis*, $2^{nd}$ ed., John Wiley and Sons, New York, 1991, pp 175–223. The selection of an appropriate protecting group can be made based upon the presence of other reactive groups in the molecule.

Subsequently, compounds of the formula V ($R^3$=H or $(C_1-C_4)$alkyl) can be converted into compounds of the formula I by subjecting them to reductive amination conditions. For example, a compound of the formula V can be reacted with a compound of the formula $HNR^1R^2$ to form an intermediate of the formula XVII:

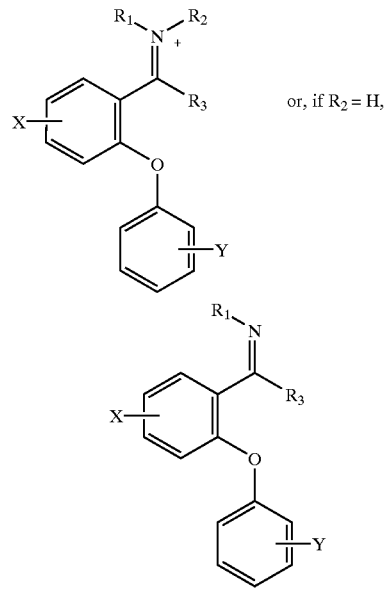

which may be isolated or converted directly in the same reaction step into a compound of the formula I. This conversion, whether in situ or starting with the isolated compound of formula XVII, can be performed using one or more methods known to those skilled in the art.

For example, the compound of formula V and the appropriate compound of formula $HNR^1R^2$ can be combined in the presence of a dehydrating reagent such as titanium (IV) tetrachloride or titanium (IV) isopropoxide, in a reaction inert solvent such as benzene, toluene, ethanol or a like solvent, until the reaction is judged to be complete, according to the procedure of S. Bhattarcharyya (*Journal of Organic Chemistry*, 1995, 60(15), 4928–4929). Alternatively, the compound of formula V and the compound of formula $HNR^1R^2$ can be combined in an inert solvent such as benzene or toluene, in the presence or absence of a water scavenger such as molecular sieves, and heated to eliminate water generated during the formation of the intermediate of formula XVII. The degree of completion of the conversion of compounds of the formula IV into the above intermediate(s) of formula XVII can be assessed using one or more known analytical techniques, including $^1$H-NMR spectroscopy.

In some instances, it may be possible or desirable to isolate the intermediate(s) of formula XVII, or they may be further reacted with a reducing agent selective for the reduction of the intermediate to the desired compounds of formula I. Such reducing agents are widely known to those skilled in the art and include, for example, sodium borohydride (NaBH$_4$), sodium cyanoborohydride (NaBH$_3$CN) and sodium triacetoxy-borohydride (NaBH(OAc)$_3$), as described by A. F. Abdel-Magid et al. in *Tetrahedron Letters*, 1990, 31, 5595. This reduction is generally carried out in a polar solvent such as methanol, ethanol, isopropanol or a like solvent, and at temperatures of about 0° C. to about 100° C., preferably at room temperature. In the procedure described by Bhattarcharyya, the intermediate of formula XVII is formed in an ethanol solvent and, without isolation, is reduced to the product of formula I using NaBH$_4$.

As an alternative to the aldehyde or ketone intermediates of formulae IV and V, one skilled in the art can also prepare compounds of formula VII (i.e., nitriles), beginning with compounds of the formulae IIIa and VI, as illustrated in Scheme 2, using the diphenyl ether formation procedure described in Scheme 1. These compounds can then serve as intermediates for the syntheses of the desired compounds of formula I. Procedures for preparation of the compounds of formula VI used in this process can be adapted from those found in the literature. (See, e.g., D. C. Remy et al., *Journal of Medicinal Chemistry*, 1975, 18(2), 142–148; E. A. Schmittling et al., *Journal of Organic Chemistry*, 1993, 58(12), 3229–3230).

The conversion of the nitriles of formula VII so obtained into the desired products of formula I can be achieved by several routes, as depicted in Scheme 2. For example, the nitrile group of VII can be hydrolyzed under acidic conditions using methods well known to those of skill in the art, to produce a carboxylic acid derivative of formula VIII. (See, e.g., A. I. Meyers et al., Tetrahedron Letters, 1984, 25 (28), 2941; and R. W. Higgins et al., *Journal of Organic Chemistry*, 1951, 16, 1275). This carboxylic acid derivative can then be converted to a compound of the formula V (R$^3$=OH), using procedures previously described in Scheme 1 for the conversion of IV to V; subsequently compound V (R$^3$=OH) can be converted to compound V (R$^3$=NR$^1$R$^2$) and then to the compounds of formula I as described below.

Alternatively, compound VIII can be converted into a carboxamide derivative of formula IX using one or more standard methods which are disclosed in the chemical literature, e.g., via reaction of an acid halide prepared from a compound of the formula VIII with an amine of general formula HNR$^1$R$^2$ (see R. E. Kent et al., *Organic Synthesis*, Coll. Vol. III, 1955, 490; and R. M. Herbst et al., *Organic Synthesis*, Coll, Vol. II, 1943, 11 for discussions of the Schotten-Bauman reaction). These carboxamides of formula IX can then be converted to the corresponding carboxamides of formula V (R$^3$=NR$^1$R$^2$) by replacing the J substituent with the appropriate X group using conditions similar to those described for converting IV to V in Scheme 1.

The carboxamides of formulae V so prepared can then be reduced to the final products of formulae I using an appropriate reduction process. Depending on the presence of substituents X, Y and Z on the carboxamides V, this reduction can be accomplished using one or more of a variety of reagents including lithium aluminum chloride (e.g., J. Lehmann et al, *Archiv. Pharm.* (Weinheim, Ger.), 1982, 315 (11), 967; N. S. Narasimhan and P. A. Patil, *Journal of the Chemical Society, Chemical Communications*, 1987, (3), 191), diborane (H. C. Brown et al, *Journal of the American Chemical Society*, 1970, 92, 1637 and 1973, 38, 912; N. M. Moon et al, *Journal of Organic Chemistry*, 1973, 38, 2786; H. C. Brown and V. Verma, *Journal of Organic Chemistry*, 1974, 39, 1631), thexylborane/diethylaniline (A. Pelter et al, *Tetrahedron Letters*, 1978, 4715), phosphorus trichloride/toluene followed by ethanolic sodium borohydride (A. Rahman et al, *Tetrahedron Letters*, 1976, 219) or aluminum hydride (H. C. Brown et al, *Journal of the American Chemical Society*, 1966, 88, 1464; A. F. Burchat et al, *Journal of Organic Chemistry*, 1996, 61(21), 7627–7630).

The resulting carboxamides of the formula IX, wherein R$^1$ and R$^2$ are hydrogen, can also be prepared directly from the corresponding nitriles of formula VII by specific hydrolysis methods, employing, for example, hydrogen peroxide or strong aqueous alkali metal salts. (See *Chemistry & Industry*, 1961, 1987; C. R. Noller, *Organic Synthesis*, Coll. Vol. II, 1943, 586; and J. H. Hall and M. Gisler, *Journal of Organic Chemistry*, 1976, 41, 3769). Subsequently, the carboxamide derivatives of formula IX may can be converted to the carboxamide compounds of formula V (R$^3$=NR$^1$R$^2$) in the manner just described for the conversion of VIII to V.

Finally, the nitriles of formula X, obtained from the nitriles of formula VII analogously to the conversion of compounds of formulae IV to V, can be reduced to the desired compounds of general formula I, wherein R$^1$ and R$^2$ are both hydrogen, by using one of a variety of reducing agents disclosed in the chemical literature which are selective for this transformation (including catalytic hydrogenation using hydrogen gas and platinum (II) oxide, as described by J. A. Secrist, III and M. W. Logue in *Journal of Organic Chemistry*, 1972, 37, 335; hydrazine hydrate and Raney nickel in ethanol, as described by W. W. Zajac, Jr. et al. in *Journal of Organic Chemistry*, 1971, 36, 3539; and sodium trifluoroacetoxy borohydride in THF, as described by N. Umino et al. in *Tetrahedron Letters*, 1976, 2875). Such reducing agents can also include lithium aluminum hydride in a nonreactive solvent such as diethyl ether or tetrahydrofuran (see, e.g., A. C. Cope et al., *Organic Synthesis*, Coll. Vol. IV, 1963, 339, for use of lithium aluminum hydride in a diethyl ether or THF solvent).

The nitriles of formula VII may also be converted to the corresponding aldehydes of general formula IV, wherein R$^3$ is hydrogen, using reagents and conditions which are specific for this transformation, such as lithium triethoxyaluminum hydride in a solvent such as THF or diethyl ether, as described by H. C. Brown and C. P. Garg in *Journal of the American Chemical Society*, 1964, 86, 1085 and by J. Malek and M. Cerny in *Synthesis*, 1972, 217.

In addition to the methods described above in Schemes 1 and 2 for the preparation of the intermediate aldehydes and ketones of formula I, other methods exist which can provide compounds of the formula I. For example, in the procedure depicted in Scheme 3, a compound of formula XIIa,b, in which E is a hydrogen atom, can be reacted, under conditions of Friedel-Crafts acylation (e.g., AlCl$_3$/CH$_2$Cl$_2$/R$^3$COCl), to produce ketones of the formula IV or V in which R$^3$ is C$_1$–C$_4$ alkyl (C. F. H. Allen, *Organic Synthesis*, Coll. Vol. II, 3, 1943). Alternatively, an acid anhydride, i.e., (R$^3$CO)$_2$O can be reacted under similar conditions (O. Grummitt et al, *Organic Synthesis*, Coll. Vol. III, 109, 1955) to produce the intermediate compounds of formula IV or V. When it is desired to prepare compounds of formula IV or V where R$^3$ is hydrogen, said compound may be prepared from compounds of formula XIIa,b via a Vilsmeier-Haack acylation, using the methods described by E. Campaigne and W. L. Archer, *Organic Synthesis*, Coll. Vol. IV, 331, 1963 and by J. H. Wood and R. W. Bost, *Organic Synthesis*, Coll. Vol. IV, 98, 1955.

The location of the acyl group ($COR^3$) introduced in this manner can be determined by the nature and location of the J, X and/or Y substituents present, as well as by the conditions employed for the reaction. In instances where it is desirable to prepare compounds of formula IV ($R^3$=H), from XIIa (E=H), introduction of the aldehyde functional group (CHO) can also be achieved using conditions described above for the preparation of the intermediates IIa and IIb in Scheme 1. For example, preparation of compounds of the formula IV wherein $R^3$=H (i.e., aldehydes) can be achieved using one or more of the known procedures for the formylation of aromatic rings, including reacting dichloromethyl methyl ether and titanium (IV) tetrachloride in methylene chloride according to the procedure described by M. L. Mancini et al., *Synthetic Communications*, 1989, 2001–2007, or H. Chikashita et al., *Journal of Organic Chemistry*, 1991, 56, 1692.

For the preparation of compounds of the general formula I wherein $R^2$ and $R^3$ taken together with the nitrogen to which $R^2$ is attached and the carbon to which $R^3$ is attached form a nitrogen containing ring, an adaptation of the procedure described by L. S. Bleicher et al (*Journal of Organic Chemistry*, 1998, 63, 1109) can be employed, as shown in Scheme 4. Thus, an ester of the general formula V ($R^3$=O-alkyl) (an intermediate of formula XVIII), prepared by esterification of the corresponding carboxylic acid of formula V ($R^3$=OH) (also of formula XVIII), is reacted with a cyclic lactam of the general formula XXV:

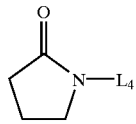

XXV where $L^4$ is a reaction labile group such as —CH=$CH_2$, in the presence of a strong base such as sodium methoxide, to produce the diketo intermediate of general formula XXI. This intermediate can then be converted to the corresponding cyclic imine of formula XXII in the presence of a strong acid, such as hydrochloric acid, usually under reflux conditions. Subsequently, the compounds of formula XXII can be reduced to form the cyclic amines of formula XXIII (wherein $R^1$=H) using, for example, sodium borohydride in methanol as described previously. Such compounds of formula XXIII can further be converted into compounds of the formula XXIII (wherein $R^1$ is as defined for compounds of formula I) as previously discussed.

For the preparation of compounds of general formula I, wherein the group X is a lactam attached to phenyl or naphthyl ring A via the lactam N atom, the method illustrated in Scheme 5 is preferred. In this procedure an aldehyde or ketone of general formula IV ($R^3$=H or $C_1$-$C_4$ alkyl, respectively) where Q is $NO_2$ is converted to an amine of the general formula XIX where $R^1$ is as previously defined, according to the method described in Scheme 1. This intermediate XIX is then converted to a compound of general formula XX, where $R^2$ is a protecting group, preferably a tert-butoxy-carbonyl (t-BOC) group, that is stable to hydrogenation conditions but can be readily removed at a later point in the synthetic sequence; suggestions for such groups can be found in Wuts and Green, supra, at page 309.

This latter intermediate XX wherein Q is $NO_2$ can then be treated under reduction conditions to form an analogous intermediate of formula XX wherein Q is $NH_2$, while leaving the t-BOC group intact. Such reduction conditions for this conversion are known to one skilled in the art and include the use of hydrogen gas ($H_2$) and a catalyst, preferably palladium on carbon, in a reaction inert solvent such as a lower alcohol (e.g., methanol, ethanol), ester (e.g., ethyl acetate), or ether (e.g., tetrahydrofuran, 1,4-dioxane) and in the presence or absence of a small amount of acid, preferably a small amount of acetic acid. The $NH_2$ group of the resulting compounds of formula XX can then be converted to cyclic amides (lactams), wherein $R^2$ remains t-BOC, by reacting them with an omega-chloro alkanoyl chloride or bromide or an omega-bromo alkanoyl chloride or bromide in a neutral solvent such as THF and in the presence of an acid scavenger, such as $Na_2CO_3$, $K_2CO_3$, $CS_2CO_3$ or the like, and heating the mixture at the boiling point of the solvent. This effects a ring closure forming the cyclic amide (i.e. lactam). Finally, the protecting group can be removed to obtain the compounds of general formula I wherein X is a lactam and R is H; in the case of the t-BOC protecting group a mixture of ethyl acetate saturated with HCl gas is effective in such removal.

Pharmaceutically acceptable salts of a compound of formula I can be prepared in a conventional manner by treating a solution or suspension of the corresponding free base or acid with one chemical equivalent of a pharmaceutically acceptable acid or base. Conventional concentration or crystallization techniques can be employed to isolate the salts. Illustrative of suitable acids are acetic, lactic, succinic, maleic, tartaric, citric, gluconic, ascorbic, benzoic, cinnamic, fumaric, sulfuric, phosphoric, hydrochloric, hydrobromic, hydroiodic, sulfamic, sulfonic acids such as methanesulfonic, benzene sulfonic, p-toluenesulfonic, and related acids. Illustrative bases are sodium, potassium, and calcium.

A compound of this invention may be administered alone or in combination with pharmaceutically acceptable carriers, in either single or multiple doses. Suitable pharmaceutical carriers include inert solid diluents or fillers, sterile aqueous solutions and various organic solvents. The pharmaceutical compositions formed by combining a compound of formula I or a pharmaceutically acceptable salt thereof can then be readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes of oral administration, tablets containing various excipients such as sodium citrate, calcium carbonate and calcium phosphate may be employed along with various disintegrants such as starch, methylcellulose, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and combinations thereof.

For parenteral administration, solutions containing a compound of this invention or a pharmaceutically acceptable salt thereof in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. The sterile aqueous media employed are all readily available by standard techniques known to those skilled in the art.

A compound of formula I or a pharmaceutically acceptable salt thereof can be administered orally, transdermally (e.g., through the use of a patch), parenterally (e.g. intravenously or rectally) or topically. In general, the daily dosage for treating a disorder or condition according to the methods described above will generally range from about 0.01 to about 10.0 mg/kg body weight of the patient to be treated. As an example, a compound of the formula I or a pharmaceutically acceptable salt thereof can be administered for treatment of, for example, depression to an adult human of average weight (about 70 kg) in a dose ranging from about 0.7 mg up to about 700 mg per day, preferably from about 1 mg to about 500 mg per day, in single or divided (i.e., multiple) portions. Variations based on the aforementioned dosage ranges may be made by a physician of ordinary skill taking into account known considerations such as the weight, age, and condition of the person being treated, the severity of the affliction, and the particular route of administration chosen.

The in vitro activity of the compounds of the present invention at the individual monoamine reuptake sites can be determined using rat synaptosomes or HEK-293 cells transfected with the human serotonin, dopamine or norepinephrine transporter, according to the following procedure adapted from those described by S. Snyder et al., (*Molecular Pharmacology,* 1971, 7, 66–80), D. T. Wong et al., (*Biochemical Pharmacology,* 1973, 22, 311–322), H. F. Bradford (*Journal of Neurochemistry,* 1969, 16, 675–684) and D. J. K. Balfour (*European Journal of Pharmacology,* 1973, 23, 19–26).

Synaptosomes: Male Sprague Dawley rats are decapitated and the brains rapidly removed. The cortex, hippocampi and corpus striata are dissected out and placed in ice cold sucrose buffer, 1 gram in 20 ml of buffer (the buffer is prepared using 320 mM sucrose containing 1 mg/ml glucose, 0.1 mM ethylenediamine tetraacetic acid (EDTA) adjusted to pH 7.4 with tris(hydroxymethyl)-aminomethane (TRIS) base). The tissues are homogenized in a glass homogenizing tube with a Teflon™ pestle at 350 rpm using a Potters homogenizer. The homogenate is centrifuged at 1000× g for 10 min. at 4° C. The resulting supernatant is recentrifuged at 17,000× g for 20 min. at 4° C. The final pellet is resuspended in an appropriate volume of sucrose buffer that yielded less than 10% uptake.

Cell Preparation: HEK-293 cells transfected with the human serotonin (5-HT), norepinephrine (NE) or dopamine (DA) transporter are grown in DMEM (Dulbecco's Modified Eagle Medium, Life Technologies Inc., 9800 Medical Center Dr., Gaithersburg, Md., catalog no. 11995–065)) supplemented with 10% dialyzed FBS (Fetal Bovine Serum, from Life Technologies, catalog no. 26300–053), 2 mM L-glutamine and 250 ug/ml G418 for the 5-HT and NE transporter or 2 ug/ml puromycin for the DA transporter, for selection pressure. The cells are grown in Gibco triple flasks, harvested with Phosphate Buffered Saline (Life Technologies, catalog no. 14190–136) and diluted to an appropriate amount to yield less than 10% uptake.

Neurotransmitter Uptake Assay: The uptake assays are conducted in glass tubes containing 50 uL of solvent, inhibitor or 10 uM sertraline, desipramine or nomifensine for the 5-HT, NE or DA assay nonspecific uptake, respectively. Each tube contains 400 uL of [3H]5-HT (5 nM final), [3H]NE (10 nM final) or [3H]DA (5 nM final) made up in modified Krebs solution containing 100 uM pargyline and glucose (1 mg/ml). The tubes are placed on ice and 50 uL of synaptosomes or cells is added to each tube. The tubes are then incubated at 37° C. for 7 min. (5-HT, DA) or 10 min. (NE). The incubation is terminated by filtration (GF/B filters), using a 96-well Brandel Cell Harvester, the filters are washed with modified Krebs buffer and counted using either a Wallac Model 1214 or Wallac Beta Plate Model 1205 scintillation counter.

Determination of the in vivo serotonin reuptake inhibition activity and potency of action for the compounds of the present invention can be made by measuring the ability of the compound to block the depletion of serotonin in the anterior cortex induced by (+/−)-para-chloroamphetamine (PCA) in the rat, according to a procedure adapted from R. W. Fuller, H. D. Snoddy and M. L. Cohen in *Neuropharmacology* 23: 539–544 (1984).

Generally, male, white Sprague-Dawley rats weighing 160–230 g each are assigned to either the control (vehicle) or test groups. When the test compound is administered subcutaneously (sc) at a given dose, it is co-administered with 5 mg/kg of para-chloroamphetamine (PCA). Three hours post-dose, the animals are sacrificed by decapitation and the anterior cortices are removed, wrapped in parafilm and frozen in dry ice (−78 C). When dosed orally (po), the rats are fasted the night before the experiment and then treated with the test compound at a given dose 30 minutes prior to the administration of the PCA (5 mg/kg, sc). After three hours, the animals are sacrificed and the tissues removed as above.

To determine the serotonin (5-HT) levels, the frozen tissues are homogenized with Branson sonifier in 0.5 mL of mobile phase in Eppendorf centrifuge tubes. Samples are then spun down at 11000 rpm for twenty minutes in a Sorval SH-MT rotor in a Sorval RC5C centrifuge. The supernatant thus obtained is pipetted into HPLC vials and the 5-HT levels are measured on HPLC-EC.

Interpretation of the results is as follows: Each experiment has a set of vehicle treated animals and a set of PCA-only animals. The mean 5-HT value of the PCA animals is subtracted from the mean 5-HT value of the vehicle animals. This is the signal or window of the response. The mean 5-HT value of each test group is determined, the mean of the PCA group subtracted from that, and that amount divided by the window is the percent protection from the PCA effect for that dose. To report an $ID_{50}$, a line is drawn mathematically through the percent protection values and the 50 percent level calculated.

All of the title compounds of formula I in the following Examples were assayed in vitro for serotonin, dopamine, and norepinephrine reuptake inhibition, and all had $IC_{50}$ values of about less than or equal to 250 nM for serotonin reuptake inhibition, about less than or equal to 1000 nM for dopamine reuptake inhibition, and about less than or equal to 1000 nM for norepinephrine reuptake inhibition.

EXAMPLES

Preparation 1

5-Bromo-2-(3,4-dichlorophenoxy)-benzaldehyde

Under $N_2$ in a 1 L round-bottomed flask fitted with a reflux condenser and magnetic stirrer were placed 51.1 g (370 mmol) of $K_2CO_3$ and 20.1 g (123 mmol) of 3,4-dichlorophenol (Aldrich Chem. Co., Milwaukee, Wis.) in 500 mL of anhydrous N,N-dimethylformamide (DMF). After stirring the mixture for 30 min., 25 g (123 mmol) of 5-bromo-2-fluoro-benzaldehyde (Aldrich) in 150 mL of DMF was added and the mixture was heated to 90–100° C. overnight. After allowing the reaction to cool to room temperature, the mixture was concentrated at reduced pressure on a rotary evaporator and the resulting oily residue was then diluted with water and EtOAc. The aqueous layer was then extracted with additional EtOAc and the organic layers were combined, washed with $H_2O$ and saturated NaCl and dried over $Na_2SO_4$. Removal of the solvent in vacuo gave a light yellow oil which was further dried under vacuum overnight to give the title product as a pale yellow solid, 40.2 g; m.p. 129–132° C.

$^1$H-NMR (CDCl$_3$, 400 MHz): δ 10.4 (s, 1H), 8.03 (d, 1H), 7.64 (dd, 1H), 7.45 (dd, 1H), 7.15 (d, 1H), 6.91 (dd, 1H), 6.89 (dd, 1H).

Mass spectrum (GCMS, m/z): 344 (m$^+$), 346.

In the same manner, reaction of 12.06 g of 4-bromo-2-fluorobenzaldehyde and 9.68 g of 3,4-dichlorophenol gave 9.64 g of 4-bromo-2-(3,4-dichlorophenoxy)-benzaldehyde as pale yellow crystals.

$^1$H-NMR (CDCl$_3$, 400 MHz): δ 10.37 (s, 1H), 7.79 (dd, 1H), 7.47 (m, 1H), 7.37 (m, 1H), 7.19 (m, 1H), 7.03 (m, 1H), 6.94 (m, 1H).

Mass spectrum (GCMS, m/z): 346 (m$^{+2}$), 344 (m$^+$).

Preparation 2

2-(3,4-Dichlorophenoxy)-5-phenyl-benzaldehyde

Under $N_2$ in a 50 mL round bottomed flask fitted with a magnetic stirrer were placed the following reactants in order: 15 mL of toluene, 500 mg (1.4 mmol) of 5-bromo-2-(3,4-dichlorophenoxy)-benzaldehyde (from Prepartion 1), 341 mg (2.8 mmol) of phenylboronic acid (Aldrich Chem. Co.), 1.5 mL of ethanol and 774 mg (5.6 mmol) of $Na_2CO_3$ in 3 mL of water. To this was added 45 mg (0.04 mmol) of tetrakis(triphenylphosphine)palladium (0) (Aldrich Chem. Co.), and the mixture was degassed with $N_2$. The reaction was next heated to reflux for 4 hr, at which time a thin layer chromatography (tlc), using 1:1 $CH_2Cl_2$: hexane on silica gel coated plates, showed the absence of the starting aldehyde. After cooling, the mixture was diluted with 100 mL of EtOAc, washed twice with water, twice with 2 N NaOH, twice with water and finally with saturated aqueous NaCl. After drying over $MgSO_4$, the solvent was removed in vacuo to give an oily residue, 690 mg. This was chromatographed on silica gel, eluting with $CH_2Cl_2$:hexane (1:1) to give the title product as an oil, 462 mg.

$^1$H-NMR (CDCl$_3$, 400 MHz): δ 10.45 (s, 1H), 8.16 (m, 1H), 7.78 (m, 1H), 7.59 (m, 2H), 7.45 (m, 3H), 7.37 (m, 1H), 7.20 (m, 1H), 7.00 (dd, 1H), 6.96 (m, 1H).

Mass spectrum (GCMS, m/z): 344 (m$^{+2}$), 342 (m$^+$).

In the same manner the following 4- or 5-substituted 2-(3,4-dichlorophenoxy) benzaldehydes were prepared:

| Prep. No. | $X_{(n)}$ | $Y_{(m)}$ | $R^3$ | yield (%) | m.p. (° C.) | m/z (m$^+$) | $^1$H-NMR (CDCl$_3$, δ) |
|---|---|---|---|---|---|---|---|
| 3 | 4-(phenyl) | 3,4-Cl$_2$ | H | 99 | oil | 342 | 10.41 (s, 1H), 8.01 (d, 1H), 7.45 (m, 7H), 7.20 (s, 1H), 7.12 (s, 1H), 6.95 (m, 1H). |
| 4 | 5-(4-methyl-phenyl) | 3,4-Cl$_2$ | H | 99 | 139–141 | 356 | 10.44 (s, 1H), 8.14 (d, 1H), 7.76 (dd, 1H), 7.46 (m, 3H), 7.22 (m, 2H), 6.96 (m, 2H), 2.39 (s, 3H). |
| 5 | 4-(4-methyl-phenyl) | 3,4-Cl$_2$ | H | 99 | White solid | 356 | 10.39 (s, 1H), 7.99 (d, 1H), 7.44 (m, 4H), 7.24 (m, 2H), 7.19 (d, 1H). 7.00 (d, 1H), 6.94 (dd, 1H), 2.78 (s, 3H). |
| 6 | 5-(4-fluoro-phenyl) | 3,4-Cl$_2$ | H | 85 | Oil | 360 | 10.44 (s, 1H), 8.10 (m, 1H), 7.72 (m, 1H), 7.53 (m, 2H), 7.46 (m, 1H), 7.18 (m, 1H), 7.13 (m, 2H), 6.97 (m, 2H). |
| 7 | 4-(4-fluoro-phenyl) | 3,4-Cl$_2$ | H | 72 | 102–106 | 360 | 10.40 (s, 1H), 8.00 (dd, 1H), 7.46 (m, 4H), 7.19 (dd, 1H), 7.12 (m, 2H), 7.06 (s, 1H), 6.94 (dd, 1H). |
| 8 | 5-(4-chloro-phenyl) | 3,4-Cl$_2$ | H | 73 | 134–138 | 376 | 10.45 (s, 1H), 8.12 (d, 1H), 7.73 (dd, 1H), 7.46 (m, 5H), 7.19 (d, 1H), 6.99 (m, 2H). |
| 9 | 4-(4-chloro-phenyl) | 3,4-Cl$_2$ | H | 98 | 157–160 | 376 | 10.40 (s, 1H), 8.00 (d, 1H), 7.42 (m, 6H), 7.19 (d, 1H), 7.07 (d, 1H), 6.94 (dd, 1H). |
| 10 | 5-(4-methoxy-phenyl) | 3,4-Cl$_2$ | H | 65 | 104–106 | 372 | 10.43 (s, 1H), 8.11 (d, 1H), 7.74 (dd, 1H). 7.48 (m, 2H), 7.44 (d, 1H), 7.17 (d, 1H), 6.96 (m, 4H). |

-continued

| Prep. No. | $X_{(n)}$ | $Y_{(m)}$ | $R^3$ | yield (%) | m.p. (° C.) | m/z ($m^+$) | $^1$H-NMR (CDCl$_3$, δ) |
|---|---|---|---|---|---|---|---|
| 11 | 4-(4-methoxyphenyl) | 3,4-Cl$_2$ | H | 74 | <100 | 372 | 10.38 (s, 1H), 7.98 (d, 1H), 7.46 (m, 4H), 7.19 (d, 1H), 7.08 (d, 1H), 6.96 (m, 3H), 3.84 (s, 3H). |
| 12 | 5-(3-acetylamino)-phenyl | 3,4-Cl$_2$ | H | 89 | oil | 400 | Not determined |
| 13 | 5-(3-thienyl) | 3,4-Cl$_2$ | H | 65 | <100 | 348 | 10.43 (s, 1H), 8.15 (m, 1H), 7.78 (m, 1H), 7.44 (m, 4H), 7.18 (m, 1H), 6.96 (m, 2H). |
| 14 | 5-(2-thienyl) | 3,4-Cl$_2$ | H | 88 | <100 | 348 | 10.46 (s, 1H), 8.15 (d, 1H), 7.77 (d, 1H), 7.44 (d, 1H), 7.29 (m, 2H), 7.18 (d, 1H), 7.09 (g, 1H), 6.96 (m, 2H). |
| 15 | 4-(3-thienyl) | 3,4-Cl$_2$ | H | 98 | <100 | 348 | 10.40 (s, 1H), 7.97 (d, 1H), 7.51 (m, 2H), 7.42 (m, 2H), 7.32 (dd, 1H), 7.18 (d, 1H), 7.12 (d, 1H), 6.94 (dd, 1H). |
| 16 | 4-(2-thienyl) | 3,4-Cl$_2$ | H | 98 | Oil | 348 | 10.34 (s, 1H), 7.95 (d, 1H), 7.51 (m, 1H), 7.44 (d, 1H), 7.37 (m, 2H), 7.18 (d, 1H), 7.13 (d, 1H), 7.09 (dd, 1H), 6.94 (dd, 1H). |
| 17 | 5-(2-turanyl) | 3,4-Cl$_2$ | H | 89 | Oil | 332 | 10.41 (s, 1H), 8.19 (d, 1H), 7.84 (d, 1H), 7.45 (m, 2H), 7.16 (d, 1H), 6.94 (m, 2H), 6.68 (d, 1H), 6.48 (m, 1H). |
| 18 | 5-(3-pyridyl) | 3,4-Cl$_2$ | H | 71 | Oil | 344 | 10.42 (s, 1H), 8.84 (s, 1H), 8.62 (dd, 1H), 8.15 (d, 1H), 7.89 (m, 1H), 7.77 (dd, 1H), 7.45 (d, 1H), 7.39 (dd, 1H), 7.21 (d, 1H), 7.04 (d, 1H), 6.97 (dd, 1H). |
| 19 | 5-(4-pyridyl) | 3,4-Cl$_2$ | H | 80 | Oil | 344 | 10.37 (s, 1H), 8.54 (m, 2H), 8.10 (d, 1H), 7.72 (q, 1H), 7.53 (m, 2H), 7.38 (m, 2H), 7.12 (d, 1H), 6.90 (m, 2H). |

Preparation 20

5-(2-Pyridyl)benzaldehyde

Under N$_2$ in a flame-dried 25 mL round bottomed flask fitted with a magnetic stirrer was placed 200 mg (0.58 mmol) of 5-bromo-2-(3,4-dichlorophenoxy)benzaldehyde, 162 mg (0.64 mmol) of bis(pinacolato)diboron (Frontier Scientific Co.), 170 mg (1.7 mmol) of potassium acetate and 13 mg (0.018 mmol) of dichloro [1,1'-bis(diphenylphosphino)ferrocene]palladium (II) dichloromethane adduct (PdCl$_2$(dppf), Strem Chemicals) in 5 mL of anhydrous DMF. The mixture was degassed with N$_2$ for 5 min. and then heated at 80° C. for 2.5 hr. To this was added 110 μL (1.2 mmol) of 2-bromopyridine, followed by 13 mg of PdCl$_2$(dppf) and 0.7 mL of 2 N aqueous Na$_2$CO$_3$. The mixture was again heated to 80° C. under N$_2$ for a total of 10.5 hr, then allowed to cool to room temperature overnight. The mixture was partitioned between EtOAc and H$_2$O, the organic layer was washed with water, brine and dried over Na$_2$CO$_3$, then concentrated in vacuo to an oil, 359 mg. Chromatography on silica gel, eluting with a gradient system of CHCl$_3$ (100–97% and CH$_3$OH (0–3%) gave the title product as a light brown oil, 44 mg.

Mass spectrum (GCMS, m/z): 346 ($m^{+2}$), 344 ($m^+$).

Preparation 21

5-Cyano-2-(3,4-dichlorophenoxy)-benzaldehyde

Under N$_2$ in a flame-dried 3-neck round bottomed flask fitted with a reflux condenser and magnetic stirrer, a mixture of 5-bromo-2-(3,4-dichlorophenoxy)-benzaldehyde (3.0 g, 8.7 mmol), zinc (II) cyanide (1.5 g, 13 mmol) and tetrakis(triphenylphosphine) palladium (0) (1.5 g, 1.3 mmol) in anhydrous DMF (145 ml) was stirred at room temperature while degassing with N$_2$ for 5 min. After heating at approximately 80° C. for 90 min., the reaction was judged complete by thin layer chromatography (1:1 CH$_2$Cl$_2$:hexanes) and was allowed to cool to room temperature. The reaction mixture was then diluted with water and ethyl acetate and stirred another 10 min. The water layer was separated, extracted twice with EtOAc and combined with the original organic layer, and washed with an aqueous solution of Rochelle salt (potassium sodium tartrate tetrahydrate) followed by aqueous NaCl. The organic layer was dried with Na$_2$SO$_4$, filtered and concentrated in vacuo to an oil. The oil was flash chromatographed on a 5×15 cm column of silica gel (230–400 mesh), eluting with CH$_2$Cl$_2$:hexanes (1:1) to obtain the title product as a white solid, 1.5 g (60%), m.p. 122–126° C.

Mass spectrum (GC/MS, m/z): 291 (m⁺), 262.

$^1$H-NMR (CDCl$_3$,): δ 10.47 (s, 1H), 8.22 (d, 1H), 7.75 (dd, 1H), 7.53 (d, 1H), 7.25 (m, 1H), 6.98 (dd, 1H), 6.92 (d, 1H).

In the same manner, 4-cyano-2-(3,4-dichlorophenoxy)-benzaldehyde was prepared from the corresponding 4-bromo-2-(3,4-dichlorophenoxy)-benzaldehyde as a clear oil, 16%. Mass spectrum (GC/MS, m/z): 291 (m⁺). $^1$H-NMR (CDCl$_3$,): δ 10.45 (s, 1H), 8.02 (d, 1H), 7.55 (m, 2H), 7.23 (m, 1H), 7.14 (m, 1H), 6.96 (dd, 1H).

Example 1

2-(3,4-Dichlorophenoxy)-5-phenyl-N-methylbenzylamine

In a round-bottomed flask fitted with a magnetic stirrer and N$_2$ inlet was placed 1.34 mL (2.68 mmol) of methylamine (2.0 M solution in methanol, Aldrich Chemical Co.) in 8.0 mL ethanol while stirring until the solution was clear. At room temperature, 0.8 mL (2.68 mmol) of titanium (IV) isopropoxide was added via syringe, followed by 0.460 g (1.34 mmol) of 2-(3,4-dichlorophenoxy)-5-phenylbenzaldehyde in 15 mL of EtOH which was then stirred overnight. To the resulting solution was added 0.076 g (2.01 mmol) of sodium borohydride, and stirring was continued for an additional 24 hr. The reaction was then quenched with approximately 3 mL of 6N HCl and 10 mL of water, the pH was adjusted to 10.0 with saturated aqueous Na$_2$CO$_3$ and stirred another 2 hr before extracting with EtOAc. The EtOAc layer was combined with additional extracts of the water layer and the combined organics were washed with saturated aqueous NaCl, dried with Na$_2$SO$_4$ and concentrated in vacuo to an oil, 0.47 g.

Mass spectrum: (APCI, m/z): 357 (m⁺).

$^1$H-NMR (CDCl$_3$, 400 MHz): δ 9.94 (bs, 2H), 7.97 (d, 1H), 7.60 (m, 2H), 7.51 (m, 1H), (m, 5H), 7.05 (m, 1H), 6.82 (d, 1H), 4.37 (m, 2H), 2.30 (m, 3H).

The oil dissolved in anhydrous EtOAc was treated with 1.3 mL of 1 N HCl in Et$_2$O and then was stirred at room temperature, the resulting solids (0.276 mg) were filtered and washed with Et$_2$O and dried under vacuum, m.p 170–173° C.

Elemental analysis for C$_{16}$H$_{14}$Cl$_2$F$_3$NO.HCl.¼H$_2$O calculated: C, 60.17, H, 4.67, N, 3.51. Found: C, 60.17, H, 4.36, N, 3.42.

In the same manner the following compounds of formula I were prepared:

| Ex. No. | X$_{(n)}$ | Y$_{(m)}$ | R$^3$ | NR$^1$R$^2$ | mp, °C. | m/z m⁺ | Elemental Analysis formula: CHN calculated:CHN found |
|---|---|---|---|---|---|---|---|
| 2 | 4-(phenyl) | 3,4-Cl$_2$ | H | NHCH$_3$ | 186–194 | 357 | C$_{20}$H$_{17}$Cl$_2$NO · HCl: C, 60.86, H, 4.44, N, 3.53. C, 60.36, H, 4.50, N, 3.52. |
| 3 | 5-(4-methyl)-phenyl | 3,4-Cl$_2$ | H | NHCH$_3$ | 208–210 | 372, 374 | C$_{21}$H$_{19}$Cl$_2$NO · HCl · 0.5 H$_2$O: C 60.37, H, 5.07, N, 3.35. C, 60.63, H, 4.82, N, 3.33. |
| 4 | 5-(4-fluoro)-phenyl | 3,4-Cl$_2$ | H | NHCH$_3$ | 195–197 | 376, 378 | C$_{20}$H$_{16}$Cl$_2$FNO · HCl: C, 58.20, H, 4.15, N, 3.39. C, 57.92, H, 3.76, N, 3.38. |
| 5 | 5-(3-acetylamino)-phenyl | 3,4-Cl$_2$ | H | NHCH$_3$ | 156–160 | 415, 417 | C$_{22}$H$_{20}$Cl$_2$N$_2$O$_2$ · HCl: C, 58.49, H, 4.69, N, 6.20. C, 58.51, H, 4.84, N, 6.03. |
| 6 | 5-(2-furanyl) | 3,4-Cl$_2$ | H | NHCH$_3$ | 188–191 | 347, 349 | C$_{18}$H$_{15}$Cl$_2$NO$_2$ · HCl · ⅓H$_2$O: C, 55.34, H, 4.30, N, 3.59. C, 55.72, H, 4.04, N, 3.58. |
| 7 | 4-(2-furanyl) | 3,4-Cl$_2$ | H | NHCH$_3$ | 129–134 | 347, 349 | C$_{18}$H$_{15}$Cl$_2$NO$_2$ · C$_4$H$_4$O$_4$ · H$_2$O: C, 54.79, H, 4.39, N, 2.90. C, 54.47, H, 4.75, N, 3.13. |
| 8 | 5-(3-thienyl) | 3,4-Cl$_2$ | H | NHCH$_3$ | 169–172 | | C$_{18}$H$_{15}$Cl$_2$NOS · HCl: C, 53.95, H, 4.02, N, 3.58. C, 53.83, H, 3.60, N, 3.96. |
| 9 | 4-(3-thienyl) | 3,4-Cl$_2$ | H | NHCH$_3$ | 181–184 | | C$_{18}$H$_{15}$Cl$_2$NOS · HCl · 0.25H$_2$O: C, 53.35, H, 4.10, N, 3.46. C, 53.40, H, 4.12, N, 3.27. |
| 10 | 5-(2-thienyl) | 3,4-Cl$_2$ | H | NHCH$_3$ | 207–209 | | C$_{18}$H$_{15}$Cl$_2$NOS · HCl: C, 53.95, H, 4.02, N, 3.58. C, 53.91, H, 3.59, N, 3.16. |
| 11 | 4-(2-thienyl) | 3,4-Cl$_2$ | H | NHCH$_3$ | 180–183 | | C$_{18}$H$_{15}$Cl$_2$NOS · HCl: C, 53.95, H, 4.02, N, 3.58. C, 53.77, H, 3.69, N, 3.27. |

| Ex. No. | $X_{(n)}$ | $Y_{(m)}$ | $R^3$ | $NR^1R^2$ | mp, °C. | m/z m+ | Elemental Analysis formula: CHN calculated:CHN found |
|---|---|---|---|---|---|---|---|
| 12 | 5-(2-pyridyl) | 3,4-$Cl_2$ | H | $NHCH_3$ |  | 359, 361 | $C_{19}H_{16}Cl_2N_2O \cdot 2HCl \cdot H_2O$: C, 50.69, H, 4.48, N, 6.22. C, 50.33, H, 4.49, N, 6.51. |
| 13 | 5-(3-pyridyl) | 3,4-$Cl_2$ | H | $NHCH_3$ | 168–171 | 359, 361 | $C_{19}H_{16}Cl_2N_2O \cdot HCl$: C, 57.67, H, 4.33, N, 7.08. C, 57.26, H, H, 4.46, N, 6.79. |
| 14 | 5-(4-pyridyl) | 3,4-$Cl_2$ | H | $NHCH_3$ | 179–181 | 359, 361 | $C_{19}H_{16}Cl_2N_2O \cdot 2HCl \cdot H_2O$: C, 50.69, H, 4.48, N, 6.22. C, 50.82, H, H, 4.48, N, 6.11. |

Example 15

5-Bromo-2-(3,4-dichlorophenoxy)—N-methylbenzylamine

Under $N_2$, a solution of methylamine (2.9 mL, 5.8 mmol, 2.0 M solution in $CH_3OH$) in 20 mL of ethanol was treated with titanium (IV) isopropoxide (1.7 mL, 5.8 mmol) at room temperature. After 5 min., a suspension of 5-bromo-2-(3,4-dichlorophenoxy)-benzaldehyde (1.0 g, 2.9 mmol, the title compound of Preparation 1) in 20 mL of ethanol was added and stirred for 16 hr at room temperature. Sodium borohydride (0.165 g, 4.4 mmol) was then added and stirring was continued for an additional 24 hr, at which time the reaction was quenched by the addition of 5 mL of 6 N HCl and 5 mL of water, stirred for 30 min and made basic by the addition of saturated aqueous $Na_2CO_3$. The resulting mixture was extracted with EtOAc, and the organic extracts were clarified by filtration throught diatomaceous earth (d.e.), washed with saturated NaCl, dried over $Na_2CO_3$ and concentrated in vacuo to a clear oil, 0.987 mg.

Example 16

1-[4-(3,4-Dichlorophenoxy)-3-methylaminomethyl-phenyl]-1H-pyrazol-3-ylamine Dihydrochloride Under $N_2$ in a flame-dried 15 mL round bottomed flask, fitted with a magnetic stirrer were placed 318 mg (0.88 mmol) of 5-bromo-2-(3,4-dichlorophenoxy)-N-methylbenzylamine (title compound of Example 15), 1.50 g (18 mmol) of 3-aminopyrazole, 56 mg (0.88 mmol) of copper powder and 122 mg (0.88 mmol) of potassium carbonate. The mixture was heated to 130° C. for a total of one hour, cooled and stirred at room temperature overnight. The tarry residue was partitioned between EtOAc and dilute aqueous EDTA (ethylenediaminetetraacetic acid), the organic layer was washed with water and saturated aqueous NaCl, then dried over $Na_2SO_4$. After filtration the solvent was removed in vacuo to give an oil, 287 mg, which was eluted on silica gel with a gradient system of $NH_4OH:CH_3OH:CHCl_3$ (from 2:2:96 to 2:10:88). The product fractions were concentrated to an oil (110 mg) which was dissolved in 25 mL EtOAc and treated with 0.6 mL of 1 N HCl in $Et_2O$. The solids which precipitated were filtered, washed with a small amount of $Et_2O$ and dried under vacuum to give 60 mg of the title product, m.p. 225–233° C.

$^1$H-NMR (DMSO-$d_6$, 400 MHz): δ 9.49 (bs, 2H), 8.44 (s, 1H), 8.20 (s, 1H), 7.74 (d, 1H), 7.66 (d, 1H), 7.44 (d, 1H), 7.10 (dd, 1H), 6.33 (s, 1H), 4.17 (s, 2H), 2.56 (s, 3H).

Mass spectrum (APCI, m/z): 363 (m+), 365.

Elemental analysis calculated for $C_{17}H_{16}Cl_2N_4O \cdot 2HCl \cdot ⅓H_2O$: C, 46.18, H, 4.26, N, 12.67. Found: C, 46.37, H, 4.30, N, 12.30.

Example 17

[2-(3,4-Dichlorophenoxy)-5-[1,2,3]triazol-1-yl-benzyl]-methylamine Hydrochloride And

[2-(3,4-Dichlorophenoxy)-5-[1,2,3]triazol-2-yl-benzyl]-methylamine Hydrochloride A mixture of 390 mg (1.08 mmol) of 5-bromo-2-(3,4-dichlorophenoxy)-N-methylbenzylamine, 1.8 g (26 mmol) of 1,2,3-triazole, 69 mg (1.08 mmol) of copper powder and 149 mg (1.08 mmol) of potassium carbonate was heated under $N_2$ at 160° C. overnight, then allowed to cool to room temperature. The mixture was partitioned between EtOAc and dilute aqueous EDTA, the organic layer was separated, washed with water, saturated aqueous NaCl and dried over $Na_2SO_4$. Concentration in vacuo gave 1.25 g of oil which was chromatographed on silica gel, eluting with a gradient system beginning with $CHCl_3$ and ending with 2:10:88 triethylamine:$CH_3OH:CHCl_3$. Two major new products were isolated.

The first, with $R_f$=0.54 (2:10:98—$NH_4OH:CH_3OH:CHCl_3$), was converted into the hydrochloride salt of [2-(3,4-dichlorophenoxy)-5-[1,2,3]triazol-2-ylbenzyl]-methylamine, 52 mg, m.p. 235–238° C.

$^1$H-NMR (DMSO-$d_6$, 400 MHz, hydrochloride salt): δ 9.14 (bs, 2H), 8.32 (d, 1H), 8.13 (s, 2H), 8.01 (dd, 1H), 7.70 (d, 1H), 7.50 (d, 1H), 7.17 (dd, 1H), 7.10 (d, 1H), 4.25 (t, 2H), 2.59 (t, 3H).

Mass spectrum (APCI, m/z): 349 (m+), 351.

Elemental analysis calculated for $C_{16}H_{14}Cl_2N_4O \cdot HCl$: C, 49.83, H, 3.92, N, 14.53. Found: C, 49.81, H, 3.69, N, 14.41.

The second, with $R_f$=0.25 was converted into the hydrochloride of [2-(3,4-dichlorophenoxy)-5-[1,2,3]triazol-1-ylbenzyl]-methylamine, m.p. 180–185° C.

$^1$H-NMR (DMSO-$d_6$, 400 MHz, hydrochloride salt): δ 9.26 (bs, 2H), 8.78 (d, 1H), 8.31 (d, 1H), 7.98 (d, 1H), 7.89 (dd, 1H), 7.70 (d, 1H), 7.50 (d, 1H), 7.18 (dd, 1H), 7.14 (d, 1H), 4.24 (s, 2H), 2.60 (s, 3H).

Mass spectrum (APCI, m/z): 349 (m+), 351.

Elemental analysis calculated for $C_{16}H_{14}Cl_2N_4O \cdot HCl \cdot 0.75H_2O$: C, 47.86, H, 4.17, N, 15.03. Found: C, 47.90, H, 3.72, N, 15.26.

Example 18

1-[4-(3,4-Dichlorophenoxy)-3-(1-methylaminoethyl)phenyl]pyrrolidin-2-one Hydrochloride A. 5-Nitro-2-(3,4-dichlorophenoxy)-acetophenone Under $N_2$, a mixture of 2-fluoro-5-nitroacetophenone (1.24 g, 6.77 mmol, prepared according to the method found in J. Med. Chem., 1991, 28(3), 673–683), 3,4-dichlorophenol (1.15 g, 7.1 mmol), $K_2CO_3$ (2.8 g, 20.3 mmol) and 15 mL of DMF were combined and stirred at room temperature for 1 hr. At this point, a tlc (40% EtOAc: 60% hexanes) indicated that the reaction was complete. The reaction was quenched with 50 mL of water and extracted with EtOAc. The organic extracts washed several times with water and aqueous NaCl and dried over $Na_2SO_4$. After filtration, the solvent was removed in vacuo to give 2.14 g of a yellow solid which was purified by flash chromatography, eluting with 10% EtOAc in hexanes. The product, 2.02 g (92%) is a white solid, m.p. 118–126° C. Mass spectrum ($M^+$): 325, 327.

B. {1-[2-(3,4-Dichlorophenoxy)-5-nitrophenyl]ethyl}-methylamine

A mixture of the preceding acetophenone resulting from step A (2.0 g, 6.1 mmol) and 2.0 M methylamine in methanol (6.1 mL, 12.2 mmol) in 25 mL of ethanol was stirred overnight at 25° C. Titanium (IV) isopropoxide (3.6 mL, 12.2 mmol) was added and the mixture was stirred another 24 hr. Sodium borohydride (0.346 g, 9.4 mmol) was then added and stirring was continued for another 24 hr, at which time a tlc (10% methanol:chloroform) indicated the reaction was complete. The reaction was quenched by adding 5 mL of 6N HCl, stirring for 20 min and then adding aqueous $NaHCO_3$ until the pH was basic. The mixture was extracted with EtOAc and the combined extracts were washed with $H_2O$, dried over $NaSO_4$, filtered and concentrated to 1.7 g of colorless oil. The oil was flash chromatographed using 2% MeOH in $CHCl_3$, and the purified product was isolated as an oil, 1.37 g.

C. {1-[2-(3,4-Dichlorophenoxy)-5-nitrophenyl]ethyl}-methylcarbamic Acid Tert-butyl Ester A solution of the preceding amine resulting from step B (1.36 g, 4 mmol) in 20 mL of $CH_2Cl_2$ was stirred with di-tert-butyldicarbonate (BOC anhydride, 0.96 g, 4.4 mmol) and triethylamine (1.2 mL, 8.6 mmol) at room temperature overnight. Removal of the solvent in vacuo gave a yellow oil, 2.04 g, which was purified using flash chromatography (15% EtOAc: hexanes) to give 1.6 g (94%) of the desired nitro intermediate as a pale yellow oil.

D. {1-[5-Amino-2-(3,4-dichlorophenoxy)phenyl]-ethyl}-methylcarbamic Acid Tert-butyl Ester The preceding nitro compound resulting from step C (0.839 g) in 20 mL of ethanol was treated with 120 mg of 10% Pd on carbon under $N_2$ and then hydrogenated on a Parr shaker apparatus at 50 psi for 25 min. The reaction was then filtered through d.e., the filter cake being washed with $CH_2Cl_2$. The combined filtrates were concentrated in vacuo to give 1.3 g of a colorless oil which was flash chromatographed, eluting with 40% EtOAc: hexanes. Concentration of the eluant fractions gave 0.62 g of the title amino intermediate of this step as a foam.

E. {1-[2-(3,4-Dichlorophenoxy)-5-(2-oxo-pyrrolidin-1-yl)phenyl]-ethyl}-methylcarbamic Acid Tert-butyl Ester The title compound of the above step D (0.615 g, 1.5 mmol) in 20 mL of anhydrous THF was combined with cesium carbonate (1.0 g, 3.1 mmol) and stirred under $N_2$ at room temperature while adding 4-chlorobutyryl chloride (0.17 mL, 1.5 mmol) via syringe. The reaction was refluxed for 24 hr, cooled to room temperature and partitioned between EtOAc and water. The organic layer was dried with $Na_2SO_4$, concentrated in vacuo to give 740 mg of solid. This solid was flash chromatographed, eluting with 40% EtOAc in hexanes to give two major fractions. The less polar fraction, 250 mg of colorless oil, was identified as the uncyclized intermediate based upon its $^1$H-nmr spectrum. The m.p. fraction, 558 mg of a white solid, was identified as the BOC-protected lactam.

$^1$H-nmr (CDCl$_3$, δ) 7.72 (bs, 1H), 7.44 (dd, 1H), 7.30 (d, 1H), 6.92 (bs, 1H), 6.89 (d, 1H), 6.73 (dd, 1H), 5.55 (bs, 1H), 3.86 (t, 2H), 2.60 (m, 5H), 2.18 (m, 2H), 1.45 (d, 3H), 1.30 (s, 9H).

F. 1-[4-(3,4-Dichlorophenoxy)-3-(1-methylaminoethyl)phenyl]-pyrrolidin-2-one Hydrochloride The title m.p. fraction from the previous step E was dissolved in 20 mL of EtOAc, cooled in an ice and acetone bath and saturated with HCl gas for approximately 5 min, then allowed to warm to room temperature overnight. The solvent was then removed in vacuo and the residue was triturated with $Et_2O$ to form white solids that were filtered and dried under vacuum, yielding 429 mg of the title hydrochloride salt as a white solid, m.p. 195–200° C. Elemental analysis calculated for $C_{19}H_{20}Cl_2N_2O_2$·HCl: C, 54.89; H, 5.09; N, 6.74. Found: C, 54.86; H, 5.40; N, 6.94

Preparation 22

[2-(3,4-Dichlorophenoxy)-5-nitrobenzyl]-methylamine

The title compound was prepared as an oil in the same manner as was the title compound of Example 18, Step B.

mass spectrum ($M^+$): 326, 328.

$^1$H-nmr (CDCl$_3$, δ) 8.36 (d, 1H), 8.08 (dd, 1H), 7.46 (d, 1H), 7.15 (d, 1H), 6.90 (dd, 1H), 6.85 (d, 1H), 3.87 (s, 2H), 2.48 (s, 3H).

Preparation 23

[2-(3,4-Dichlorophenoxy)-5-nitrobenzyl]-methylcarbamic Acid Tert-butyl Ester

The title compound was prepared as a white solid in the same manner as was the title compound of Example 18, Step C. M.p. 102–108° C.

Preparation 24

[5-Amino-2-(3,4-dichlorophenoxy)benzyl]-methylcarbamic Acid Tert-butyl Ester

The title compound was prepared as a coloroless oil in the same manner as was the title compound of Example 18, Step D.

Preparations 25 and 26

The following intermediates were prepared in the same manner as was the title compound of Example 18, Step E:

[2-(3,4-Dichlorophenoxy)-5-(2-oxo-piperidin-1-yl)benzyl]-methylcarbamic Acid Tert-butyl Ester Colorless oil, 1.82 g (76%).

[2-(3,4-Dichlorophenoxy)-5-(2-oxo-pyrrolidin-1-yl)benzyl]-methylcarbamic Acid Tert-butyl Ester Colorless oil, 0.867 g (98%).

$^1$H-nmr (CDCl$_3$, δ) 7.65 (dd, 1H), 7.41 (d, 1H), 7.33 (d, 1H), 6.96 (d, 1H), 6.92 (d, 1H), 6.75 (dd, 1H), 4.39 (bs, 2H), 3.83 (t, 2H), 2.82 (d, 3H), 2.60 (t, 2H), 2.16 (m, 2H), 1.43 (s, 9H).

The following compound were prepared in the same manner as Step F of Example 18:

Example 19

1-[4-(3,4-Dichlorophenoxy)-3-(methylaminomethyl)phenyl]-pyrrolidin-2-one

M.p. 166–170° C.

Elemental analysis calculated for $C_{18}H_{18}Cl_2N_2O_2 \cdot HCl$: C, 53.82; H, 4.77; N, 6.97. Found: C, 54.03; H, 4.80; N, 6.88.

Example 20

1-[4-(3,4-Dichlorophenoxy)-3-(methylaminomethyl)phenyl]-piperidin-2-one Hydrochloride M.p. 191–196° C.

$^1$H-nmr (free base, CDCl3, δ) 9.75 (s, 2H), 7.70 (s, 1H), 7.41 (d, 1H), 7.27 (d, 1H), 7.22 (dd, 1H), 7.04 (dd, 1H), 6.77 (d, 1H), 4.13 (s, 2H), 3.65 (t, 2H), 2.58 (t, 3H), 2.59 (t, 2H), 1.95 (m, 4H).

Elemental analysis calculated for $C_{19}H_{20}Cl_2N_2O \cdot HCl \cdot \frac{3}{4}H_2O$: C, 53.16; H, 5.28; N, 6.53. Found: C, 52.91; H, 5.28; N, 6.85.

What is claimed is:

1. A pharmaceutical composition for treating a disorder or condition selected from depression, phobias, eating disorders, obesity and obsessive-compulsive disorder in a mammal, comprising an amount of a compound of formula I or a pharmaceutically acceptable salt thereof that is effective in treating such disorder or condition, and a pharmaceutically acceptable carrier, wherein the compound of formula I is:

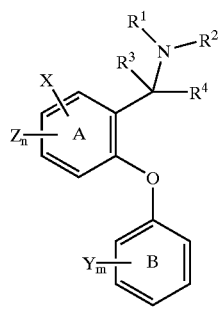

wherein phenyl ring A and phenyl ring B can each, independently, be replaced by a naphthyl group, and wherein when phenyl ring A is replaced by a naphthyl group, the ethereal oxygen of structure I and the carbon to which $R^3$, $R^4$ and $NR^1R^2$ are attached, are attached to adjacent ring carbon atoms of the naphthyl group and neither of said adjacent ring carbon atoms is also adjacent to a fused ring carbon atom of said naphthyl group;

n and m are, selected, independently, from one, two and three;

$R^1$ and $R^2$ are selected, independently, from hydrogen, $(C_1-C_4)$alkyl, $(C_2-C_4)$alkenyl, and $(C_2-C_4)$alkynyl, or $R^1$ and $R^2$, together with the nitrogen to which they are attached, form a four to eight membered saturated ring containing one or two heteroatoms, including the nitrogen to which $R^1$ and $R^2$ are attached, wherein the second heteroatom, when present, is selected from oxygen, nitrogen and sulfur, and wherein said ring may optionally be substituted at available binding sites with from one to three substituents selected, independently, from hydroxy and $(C_1-C_6)$alkyl;

$R^3$ and $R^4$ are selected, independently, from hydrogen and $(C_1-C_4)$ alkyl optionally substituted with from one to three fluorine atoms, or $R^3$ and $R^4$, together with the carbon to which they are attached, form a four to eight membered saturated carbocyclic ring, and wherein said ring may optionally be substituted at available binding sites with from one to three substituents selected, independently, from hydroxy and $(C_1-C_6)$alkyl;

or $R^2$ and $R^3$, together with the nitrogen to which $R^2$ is attached and the carbon to which $R^3$ is attached, form a four to eight membered saturated ring containing one or two heteroatoms, including the nitrogen to which $R^2$ is attached, wherein the second heteroatom, when present, is selected from oxygen, nitrogen and sulfur, and wherein said ring may optionally be substituted at available binding sites with from one to three substituents selected, independently, from hydroxy and $(C_1-C_6)$alkyl;

each X is selected, independently, from phenyl, heteroaryl and heterocycle, and wherein each X may be further substituted by hydrogen, halo, $(C_1-C_4)$alkyl optionally substituted with from one to three fluorine atoms, $(C_1-C_4)$alkoxy optionally substituted with from one to three fluorine atoms, cyano, nitro, amino, hydroxy, carbonyl, $(C_1-C_4)$alkylamino, di-[$(C_1-C_4)$alkyl]amino, $NR^5(C=O)(C_1-C_4)$alkyl, $SO_2NR^5R^6$ and $SO_p(C_1-C_6)$alkyl, wherein $R^5$ and $R_6$ are selected, independently, from hydrogen and $(C_1-C_6)$alkyl, and p is zero, one or two;

each Y is selected, independently, from hydrogen, halo, $(C_1-C_4)$alkyl optionally substituted with from one to three fluorine atoms, $(C_1-C_4)$alkoxy optionally substituted with from one to three fluorine atoms, cyano, nitro, amino, $(C_1-C_4)$alkylamino, di-[$(C_1-C_4)$alkyl]amino, $NR^5(C=O)(C_1-C_4)$alkyl, $SO_2NR^5R^6$ and $SO_p(C_1-C_6)$alkyl, wherein $R^5$ and $R^6$ are selected, independently, from hydrogen and $(C_1-C_6)$alkyl, and p is zero, one or two; and each Z is selected independently from hydrogen, halo, $(C_1-C_4)$alkyl optionally substituted with from one to three fluorine atoms, $(C_1-C_4)$alkoxy.

2. A pharmaceutical composition for treating a disorder or condition that can be treated by inhibiting the reuptake of serotonin in a mammal, comprising an amount of a compound of formula I or pharmaceutically acceptable salt thereof that is effective in treating such disorder or condition, and a pharmaceutically acceptable carrier, wherein the compound of formula I is:

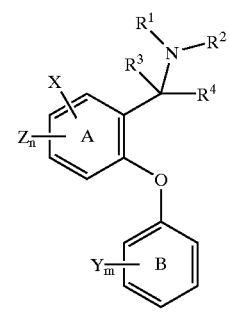

wherein phenyl ring A and phenyl ring B can each, independently, be replaced by a naphthyl group, and wherein when phenyl ring A is replaced by a naphthyl group, the ethereal oxygen of structure I and the carbon to which $R^3$, $R^4$ and $NR^1R^2$ are attached, are attached to adjacent ring carbon atoms of the naphthyl group and neither of said adjacent ring carbon atoms is also adjacent to a fused ring carbon atom of said naphthyl group;

n and m are, selected, independently, from one, two and three;

$R^1$ and $R^2$ are selected, independently, from hydrogen, $(C_1-C_4)$alkyl, $(C_2-C_4)$alkenyl, and $(C_2-C_4)$alkynyl, or $R^1$ and $R^2$, together with the nitrogen to which they are attached, form a four to eight membered saturated ring containing one or two heteroatoms, including the nitrogen to which $R^1$ and $R^2$ are attached, wherein the second heteroatom, when present, is selected from oxygen, nitrogen and sulfur, and wherein said ring may optionally be substituted at available binding sites with from one to three substituents selected, independently, from hydroxy and $(C_1-C_6)$alkyl;

$R^3$ and $R^4$ are selected, independently, from hydrogen and $(C_1-C_4)$ alkyl optionally substituted with from one to three fluorine atoms, or $R^3$ and $R^4$, together with the carbon to which they are attached, form a four to eight membered saturated carbocyclic ring, and wherein said ring may optionally be substituted at available binding sites with from one to three substituents selected, independently, from hydroxy and $(C_1-C_6)$alkyl;

or $R^2$ and $R^3$, together with the nitrogen to which $R^2$ is attached and the carbon to which $R^3$ is attached, form a four to eight membered saturated ring containing one or two heteroatoms, including the nitrogen to which $R^2$ is attached, wherein the second heteroatom, when present, is selected from oxygen, nitrogen and sulfur, and wherein said ring may optionally be substituted at available binding sites with from one to three substituents selected, independently, from hydroxy and $(C_1-C_6)$alkyl;

each X is selected, independently, from phenyl, heteroaryl and heterocycle, and wherein each X may be further substituted by hydrogen, halo, $(C_1-C_4)$alkyl optionally substituted with from one to three fluorine atoms, $(C_1-C_4)$alkoxy optionally substituted with from one to three fluorine atoms, cyano, nitro, amino, hydroxy, carbonyl, $(C_1-C_4)$alkylamino, di-$[(C_1-C_4)$alkyl]amino, $NR^5(C=O)(C_1-C_4)$alkyl, $SO_2NR^5R^6$ and $SO_p(C_1-C_6)$ alkyl, wherein $R^5$ and $R^6$ are selected, independently, from hydrogen and $(C_1-C_6)$alkyl, and p is zero, one or two;

each Y is selected, independently, from hydrogen, halo, $(C_1-C_4)$alkyl optionally with from one to three fluorine atoms, $(C_1-C_4)$alkoxy optionally substituted substituted with from one to three fluorine atoms, cyano, nitro, amino, $(C_1-C_4)$alkylamino, di-$[(C_1-C_4)$alkyl]amino, $NR^5(C=O)(C_1-C_4)$alkyl, $SO_2NR^5R^6$ and $SO_p(C_1-C_6)$alkyl, wherein $R^5$ and $R^6$ are selected, independently, from hydrogen and $(C_1-C_6)$alkyl, and p is zero, one or two; and each Z is selected independently from hydrogen, halo, $(C_1-C_4)$alkyl optionally substituted with from one to three fluorine atoms, $(C_1-C_4)$alkoxy.

3. A method for treating a disorder or condition selected from depression, phobias, eating disorders, obesity and obsessive-compulsive disorder in a mammal, comprising administering to a mammal in need of such treatment an amount of a compound of formula I or a pharmaceutically acceptable salt thereof that is effective in treating such disorder or condition, wherein the compound of formula I is:

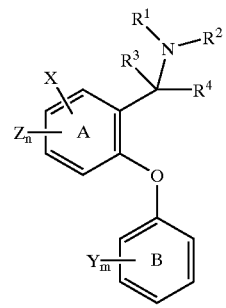

I wherein phenyl ring A and phenyl ring B can each, independently, be replaced by a naphthyl group, and wherein when phenyl ring A is replaced by a naphthyl group, the ethereal oxygen of structure I and the carbon to which $R^3$, $R^4$ and $NR^1R^2$ are attached, are attached to adjacent ring carbon atoms of the naphthyl group and neither of said adjacent ring carbon atoms is also adjacent to a fused ring carbon atom of said naphthyl group;

n and m are, selected, independently, from one, two and three;

$R^1$ and $R^2$ are selected, independently, from hydrogen, $(C_1-C_4)$alkyl, $(C_2-C_4)$alkenyl, and $(C_2-C_4)$alkynyl, or $R^1$ and $R^2$, together with the nitrogen to which they are attached, form a four to eight membered saturated ring containing one or two heteroatoms, including the nitrogen to which $R^1$ and $R^2$ are attached, wherein the second heteroatom, when present, is selected from oxygen, nitrogen and sulfur, and wherein said ring may optionally be substituted at available binding sites with from one to three substituents selected, independently, from hydroxy and $(C_1-C_6)$alkyl;

$R^3$ and $R^4$ are selected, independently, from hydrogen and $(C_1-C_4)$ alkyl optionally substituted with from one to three fluorine atoms, or $R^3$ and $R^4$, together with the carbon to which they are attached, form a four to eight membered saturated carbocyclic ring, and wherein said ring may optionally be substituted at available binding sites with from one to three substituents selected, independently, from hydroxy and $(C_1-C_6)$alkyl;

or $R^2$ and $R^3$, together with the nitrogen to which $R^2$ is attached and the carbon to which $R^3$ is attached, form a four to eight membered saturated ring containing one or two heteroatoms, including the nitrogen to which $R^2$ is attached, wherein the second heteroatom, when present, is selected from oxygen, nitrogen and sulfur, and wherein said ring may optionally be substituted at available binding sites with from one to three substituents selected, independently, from hydroxy and $(C_1-C_6)$alkyl;

each X is selected, independently, from phenyl, heteroaryl and heterocycle, and wherein each X may be further substituted by hydrogen, halo, $(C_1-C_4)$alkyl optionally substituted with from one to three fluorine atoms, $(C_1-C_4)$alkoxy optionally substituted with from one to three fluorine atoms, cyano, nitro, amino, hydroxy, carbonyl, $(C_1-C_4)$alkylamino, di-$[(C_1-C_4)$alkyl]amino, $NR^5(C=O)(C_1-C_4)$alkyl, $SO_2NR^5R^6$ and $SO_p(C_1-C_6)$ alkyl, wherein $R^5$ and $R^6$ are selected, independently, from hydrogen and $(C_1-C_6)$alkyl, and p is zero, one or two;

each Y is selected, independently, from hydrogen, halo, $(C_1-C_4)$alkyl optionally substituted with from one to three fluorine atoms, (C₁–C₄)alkoxy optionally substituted with from one to three fluorine atoms, cyano, nitro, amino, (C₁–C₄)alkylamino, di-[(C₁–C₄)alkyl]amino, NR⁵(C=O)(C₁–C₄)alkyl, SO₂NR⁵R⁶ and SO$_p$(C₁–C₆)alkyl, wherein R⁵ and R⁶ are selected, independently, from hydrogen and (C₁–C₆)alkyl, and p is zero, one or two; and each Z is selected independently from hydrogen, halo, (C₁–C₄)alkyl optionally substituted with from one to three fluorine atoms, (C₁–C₄)alkoxy.

4. A method for treating a disorder or condition that can be treated by inhibiting the reuptake of serotonin in a mammal, comprising administering to a mammal in need of such treatment an amount of a compound of formula I or a pharmaceutically acceptable salt thereof that is effective in treating such disorder or condition, wherein the compound of formula I is:

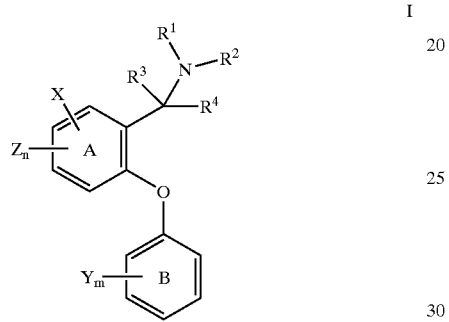

I wherein phenyl ring A and phenyl ring B can each, independently, be replaced by a naphthyl group, and wherein when phenyl ring A is replaced by a naphthyl group, the ethereal oxygen of structure I and the carbon to which R³, R⁴ and NR¹R² are attached, are attached to adjacent ring carbon atoms of the naphthyl group and neither of said adjacent ring carbon atoms is also adjacent to a fused ring carbon atom of said naphthyl group;

n and m are, selected, independently, from one, two and three;

R¹ and R² are selected, independently, from hydrogen, (C₁–C₄)alkyl, (C₂–C₄)alkenyl, and (C₂–C₄)alkynyl, or R¹ and R², together with the nitrogen to which they are attached, form a four to eight membered saturated ring containing one or two heteroatoms, including the nitrogen to which R¹ and R² are attached, wherein the second heteroatom, when present, is selected from oxygen, nitrogen and sulfur, and wherein said ring may optionally be substituted at available binding sites with from one to three substituents selected, independently, from hydroxy and (C₁–C₆)alkyl;

R³ and R⁴ are selected, independently, from hydrogen and (C₁–C₄) alkyl optionally substituted with from one to three fluorine atoms, or R³ and R⁴, together with the carbon to which they are attached, form a four to eight membered saturated carbocyclic ring, and wherein said ring may optionally be substituted at available binding sites with from one to three substituents selected, independently, from hydroxy and (C₁–C₆)alkyl;

or R² and R³, together with the nitrogen to which R² is attached and the carbon to which R³ is attached, form a four to eight membered saturated ring containing one or two heteroatoms, including the nitrogen to which R² is attached, wherein the second heteroatom, when present, is selected from oxygen, nitrogen and sulfur, and wherein said ring may optionally be substituted at available binding sites with from one to three substituents selected, independently, from hydroxy and (C₁–C₆)alkyl;

each X is selected, independently, from phenyl, heteroaryl and heterocycle, and wherein each X may be further substituted by hydrogen, halo, (C₁–C₄)alkyl optionally substituted with from one to three fluorine atoms, (C₁–C₄)alkoxy optionally substituted with from one to three fluorine atoms, cyano, nitro, amino, hydroxy, carbonyl, (C₁–C₄)alkylamino, di-[(C₁–C₄)alkyl]amino, NR⁵(C=O)(C₁–C₄)alkyl, SO₂NR⁵R⁶ and SO$_p$(C₁–C₆) alkyl, wherein R⁵ and R⁶ are selected, independently, from hydrogen and (C₁–C₆)alkyl, and p is zero, one or two;

each Y is selected, independently, from hydrogen, halo, (C₁–C₄)alkyl optionally substituted with from one to three fluorine atoms, (C₁–C₄)alkoxy optionally substituted with from one to three fluorine atoms, cyano, nitro, amino, (C₁–C₄)alkylamino, di-[(C₁–C₄)alkyl]amino, NR⁵(C=O)(C₁–C₄)alkyl, SO₂NR⁵R⁶ and SO$_p$(C₁–C₆)alkyl, wherein R⁵ and R⁶ are selected, independently, from hydrogen and (C₁–C₆)alkyl, and p is zero, one or two; and each Z is selected independently from hydrogen, halo, (C₁–C₄)alkyl optionally substituted with from one to three fluorine atoms, (C₁–C₄)alkoxy.

* * * * *